(12) United States Patent
Sharma et al.

(10) Patent No.: US 11,903,595 B2
(45) Date of Patent: Feb. 20, 2024

(54) SURGICAL ALIGNMENT BY MAGNETIC FIELD GRADIENT LOCALIZATION

(71) Applicant: CALIFORNIA INSTITUTE OF TECHNOLOGY, Pasadena, CA (US)

(72) Inventors: Saransh Sharma, Pasadena, CA (US); Abhinav Agarwal, Pasadena, CA (US); Mikhail Shapiro, Pasadena, CA (US); Azita Emami, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 17/813,177

(22) Filed: Jul. 18, 2022

(65) Prior Publication Data
US 2022/0346811 A1    Nov. 3, 2022

Related U.S. Application Data

(62) Division of application No. 16/409,727, filed on May 10, 2019, now Pat. No. 11,399,848.

(60) Provisional application No. 62/688,235, filed on Jun. 21, 2018.

(51) Int. Cl.
*A61B 17/17* (2006.01)
*G01B 7/31* (2006.01)

(52) U.S. Cl.
CPC ...... *A61B 17/1707* (2013.01); *A61B 17/1725* (2013.01); *G01B 7/31* (2013.01)

(58) Field of Classification Search
CPC .................................................. A61B 17/1707
See application file for complete search history.

(56) References Cited

U.S. PATENT DOCUMENTS

| | | | | |
|---|---|---|---|---|
| 5,558,091 | A * | 9/1996 | Acker | A61B 5/103 324/207.13 |
| 11,399,848 | B2 | 8/2022 | Sharma et al. | |
| 2004/0116772 | A1* | 6/2004 | Lupin | H04R 25/606 600/25 |
| 2004/0243211 | A1* | 12/2004 | Colliou | A61N 1/36007 607/133 |
| 2005/0070916 | A1* | 3/2005 | Hollstien | A61B 17/1707 606/96 |
| 2007/0244388 | A1 | 10/2007 | Sato et al. | |

(Continued)

FOREIGN PATENT DOCUMENTS

| | | |
|---|---|---|
| KR | 20070086118 A | 8/2007 |
| KR | 20120027252 A | 3/2012 |
| KR | 20140082686 A | 7/2014 |

OTHER PUBLICATIONS

Communication Under Rule 71(3) EPC issued for European Patent Application 19822267.1 filed on Dec. 22, 2020 on behalf of California Institute of Technology. Dated Oct. 2, 2023. 58 pages.

(Continued)

*Primary Examiner* — Nicholas W Woodall
(74) *Attorney, Agent, or Firm* — Steinfl+Bruno LLP

(57) ABSTRACT

A three dimensional magnetic sensor attached to a surgical nail is located based on an applied monotonic magnetic field gradient. Another three dimensional magnetic sensor locates a surgical drill. A display generates a real time image of the relative alignment of the surgical drill and of the surgical nail, allowing a surgeon to repair bone fractures.

11 Claims, 28 Drawing Sheets

(56) References Cited

U.S. PATENT DOCUMENTS

| | | |
|---|---|---|
| 2012/0035468 A1 | 2/2012 | Ritchey et al. |
| 2012/0226094 A1* | 9/2012 | Ritchey .............. A61B 17/1707 606/62 |
| 2015/0080710 A1 | 3/2015 | Henkel et al. |
| 2016/0157751 A1* | 6/2016 | Mahfouz .................. A61B 6/12 600/409 |

OTHER PUBLICATIONS

Notice to File Response issued for KR application No. 10-2020-7036163 filed on Dec. 15, 2020 on behalf of California Institute of Technology. Dated Sep. 6, 2023. 12 pages. English Translation + KR Original.

* cited by examiner

SURGICAL ALIGNMENT BY MAGNETIC FIELD GRADIENT LOCALIZATION

CROSS REFERENCE TO RELATED APPLICATIONS

The present application is a divisional application of U.S. Non-Provisional application Ser. No. 16/409,727, filed on May 10, 2019, which claims priority to U.S. Provisional Application No. 62/688,235, filed on Jun. 21, 2018, the contents of each which are incorporated herein by reference in their entirety.

TECHNICAL FIELD

The present disclosure relates to magnetic sensors. More particularly, it relates to surgical alignment by magnetic field gradient localization.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
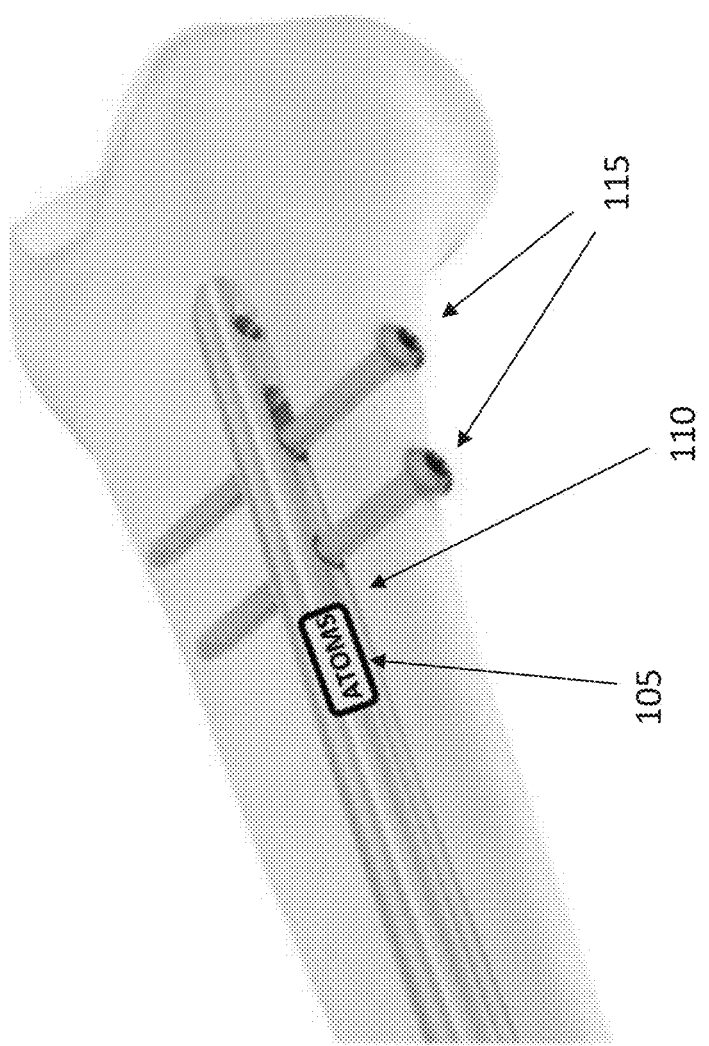
FIG. 1 illustrates a nail in a bone.

In a first aspect of the disclosure, a system is described, the system comprising: a first sensor configured to be inserted in a patient during a surgical procedure, the first sensor comprising: a first magnetic sensor configured to detect a first magnetic field value, a first integrated circuit chip configured to process data from the first magnetic sensor, and a first radiofrequency coil configured to transmit data processed by the first integrated circuit chip based on the first magnetic field; a second sensor attached to a surgical instrument, the second sensor comprising: a second magnetic sensor configured to detect a second magnetic field value, and a second integrated circuit chip configured to process data from the second magnetic sensor; and a plurality of coils configured to generate a magnetic field gradient within a volume in which the surgical procedure takes place, wherein the magnetic field gradient has a unique field value at each spatial location.

In a second aspect of the disclosure, a system is described, the system comprising: a first sensor configured to be inserted in a patient during a surgical procedure, the first sensor comprising: a magnetic sensor configured to detect a first magnetic field value, an integrated circuit chip configured to process data from the magnetic sensor, and a radiofrequency coil configured to transmit data processed by the integrated circuit chip based on the first magnetic field; a surgical instrument; a second sensor configured to sense a location of the surgical instrument relative to the first sensor; and a plurality of coils configured to generate a magnetic field gradient within a volume in which the surgical procedure takes place, wherein the magnetic field gradient has a unique field value at each spatial location.

In a third aspect of the disclosure, a method is described, the method comprising: providing a system comprising: a first sensor configured to be inserted in a patient during a surgical procedure, the first sensor comprising: a first magnetic sensor configured to detect a first magnetic field value, a first integrated circuit chip configured to process data from the first magnetic sensor, and a first radiofrequency coil configured to transmit data processed by the first integrated circuit chip based on the first magnetic field; a second sensor attached to a surgical instrument, the second sensor comprising: a second magnetic sensor configured to detect a second magnetic field value, and a second integrated circuit chip configured to process data from the second magnetic sensor; generating, by a plurality of coils, a magnetic field gradient within a volume in which the surgical procedure takes place, wherein the magnetic field gradient has a unique field value at each spatial location; sensing, by the first sensor, a first location of the first sensor based on the magnetic field gradient; sensing, by the second sensor, a second location of the second sensor based on the magnetic field gradient; displaying, on a display, the first and second locations, and a relative alignment between the first location and the second location; and aligning the surgical instrument based on the displayed relative alignment.

In a fourth aspect of the disclosure, a method is described, the method comprising providing a system comprising: a first sensor configured to be inserted in a patient during a surgical procedure, the first sensor comprising: a magnetic sensor configured to detect a first magnetic field value, an integrated circuit chip configured to process data from the magnetic sensor, and a radiofrequency coil configured to transmit data processed by the integrated circuit chip based on the first magnetic field; a surgical instrument; and a second sensor configured to sense a location of the surgical instrument relative to the first sensor; generating, by a plurality of coils, a magnetic field gradient within a volume in which the surgical procedure takes place, wherein the magnetic field gradient has a unique field value at each spatial location; sensing, by the first sensor, a first location of the first sensor based on the magnetic field gradient; sensing, by the second sensor, a location of the surgical instrument relative to the first sensor; displaying, on a display, the first and second locations, and a relative alignment between the first location and the second location; and aligning the surgical instrument based on the displayed relative alignment.

DETAILED DESCRIPTION

The present disclosure refers to the surgical alignment of fractured bones. Intramedullary (IM) nailing is the process of treating long bone fractures. It consists of insertion of a metallic nail into the medullary canal of the fractured bone, followed by locking screws to avoid displacement of bone fragments around or along the nail. The surgical nail comprises holes to accept the screws. The screws are inserted through bone fragments into the proximal and distal holes in the nail. Proximal screw locking is performed using a mechanical guide fixed to the proximal part of the nail, and is relatively simpler than distal locking. Using such a guide is not possible for distal locking because the nail is usually deformed during its insertion into the canal, owing to the non-linearity of the bone. This deformation can be as high as 10 mm from the axis of the nail. Therefore, distal locking is the most challenging part of intramedullary nailing of femur and tibia. Additional pitfalls and complications that may occur include inadequate fixation, bone cracking, cortical wall penetration, bone weakening due to multiple or enlarged screw holes, and distal fragment mal-rotation if the drill is not perfectly aligned with the hole axis.

In order to locate the distal holes, various methods have been proposed and are used by surgeons worldwide. The most frequently used is the freehand technique in which the hole axis is determined using a surgical drill and the alignment is achieved through fluoroscopic imaging. The fluoroscopic device is positioned perpendicular to each distal hole so that it appears perfectly circular on the screen. This alignment procedure is time-consuming and exposes the patient and the surgical team to high irradiation. The surgeon's direct radiation exposure varies from 3.1 min to 31.4 min, with the distal locking itself causing 31%-51% of the total irradiation per nailing operation. Moreover, the free hand technique requires the expertise of both the surgeon and the X-ray technician; it has a slow learning curve, and it is largely dependent on the image intensifier.

Various other methods which minimize or completely eliminate irradiation during distal locking have been proposed. These include hand held targeting devices and radiolucent drill guides, laser-guided systems, computer-assisted systems, image intensifier mounted targeting devices, proximally mounted distal locking devices, and electromagnetic field tracking technology. These proximally mounted targeting devices fail because their aiming arms do not compensate for a significant deformation of the nail caused during insertion. Other methods are even more complex and their successful use requires a significant learning curve for the surgeon and the staff. Moreover, additional requirements like computing system, robotic arm, computed tomography (CT) images, sophisticated hardware and software, make these propositions expensive to be implemented widely. For these reasons, the most familiar method remains the freehand technique, despite all its limitations. However, there is a clear need for alternative techniques with limited or no radiation exposure in distal locking of IM nails.

The present disclosure describes the design of a fully implantable wireless electronic device which can be used to eliminate fluoroscopic imaging in the IM nailing process, and also reduce the present surgery time since continuous monitoring to get accurate images during distal locking would no longer be required.

The present disclosure describes a wireless electronic device which can provide accurate 3D position information when a magnetic field gradient is applied across it. This device is referred to as Addressable Transmitters Operated as Magnetic Spins, abbreviated as ATOMS. The device can be placed on an IM nail right next to the distal hole, as shown in FIG. 1. FIG. 1 illustrates the ATOMS device (105) attached to the nail (110), and two screws (115) inserted within holes in the nail.

Figure 4:
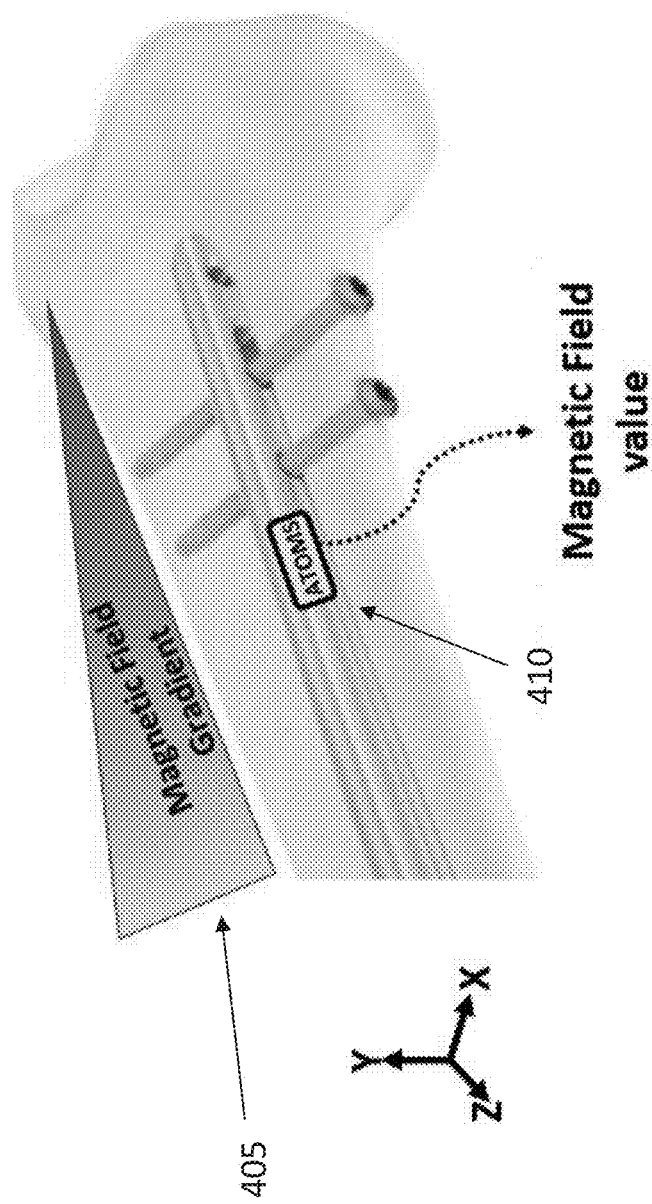
FIG. 4 illustrates an exemplary field gradient for positioning.

A 3D magnetic field gradient is applied over the distal nail position. The 3D magnetic sensor, integrated in ATOMS, senses the magnetic field at its location and transmits the corresponding value. This value, when mapped to the externally applied gradient, gives the exact position of the sensor. The schematic of the working principle is shown in FIG. 4. FIG. 4 illustrates an exemplary magnetic field gradient (405), having a varying value across the bone, which is sensed by the ATOMS (410). For example, coils can be placed under a patient's leg on an operating table, generating a magnetic field gradient within the volume of the leg.

Figure 2:
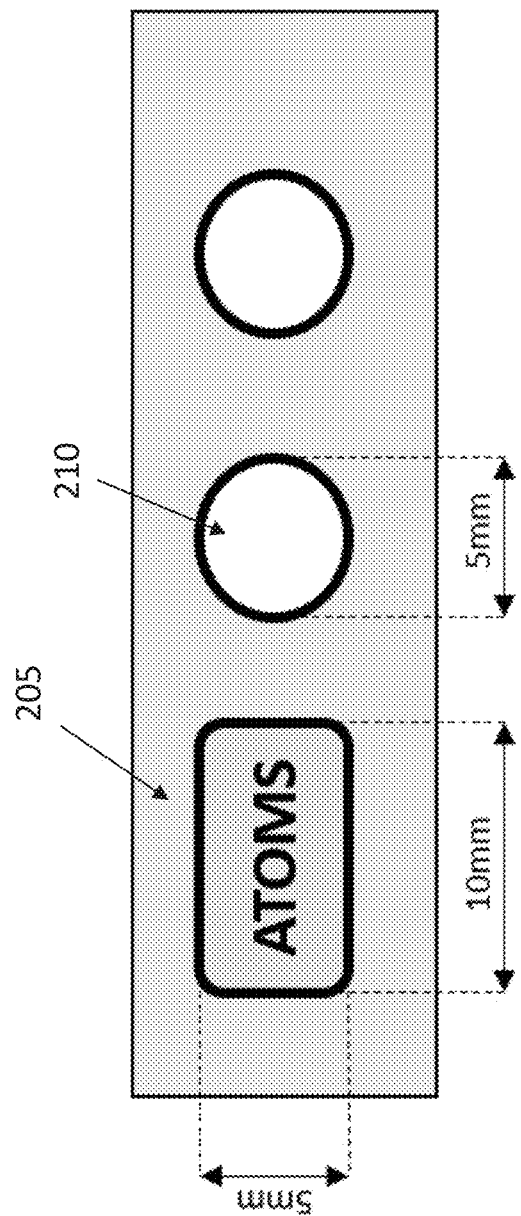
FIG. 2 illustrates typical dimensions of an ATOMS device.

FIG. 2 shows typical dimensions of an ATOMS device, compared to a hole (210) in a nail. The present disclosure describes how to provide accurate 3D navigation data from ATOMS, enabling the surgeon to obtain complete information about its position in 3D space, which is equivalent to having the distal hole's position. The drill bit which is used to create the initial opening in the bone to insert a locking screw is accurately navigated to the correct position of the targeted hole in such a way that the axis of the hole matches the axis of the drill bit. To ensure perfect alignment, another identical ATOMS is installed in the drill bit along the drilling axis. The goal is then to bring the two completely in alignment with each other, by displaying on a computer screen the real time position of both of the ATOMS devices.

Figure 3:
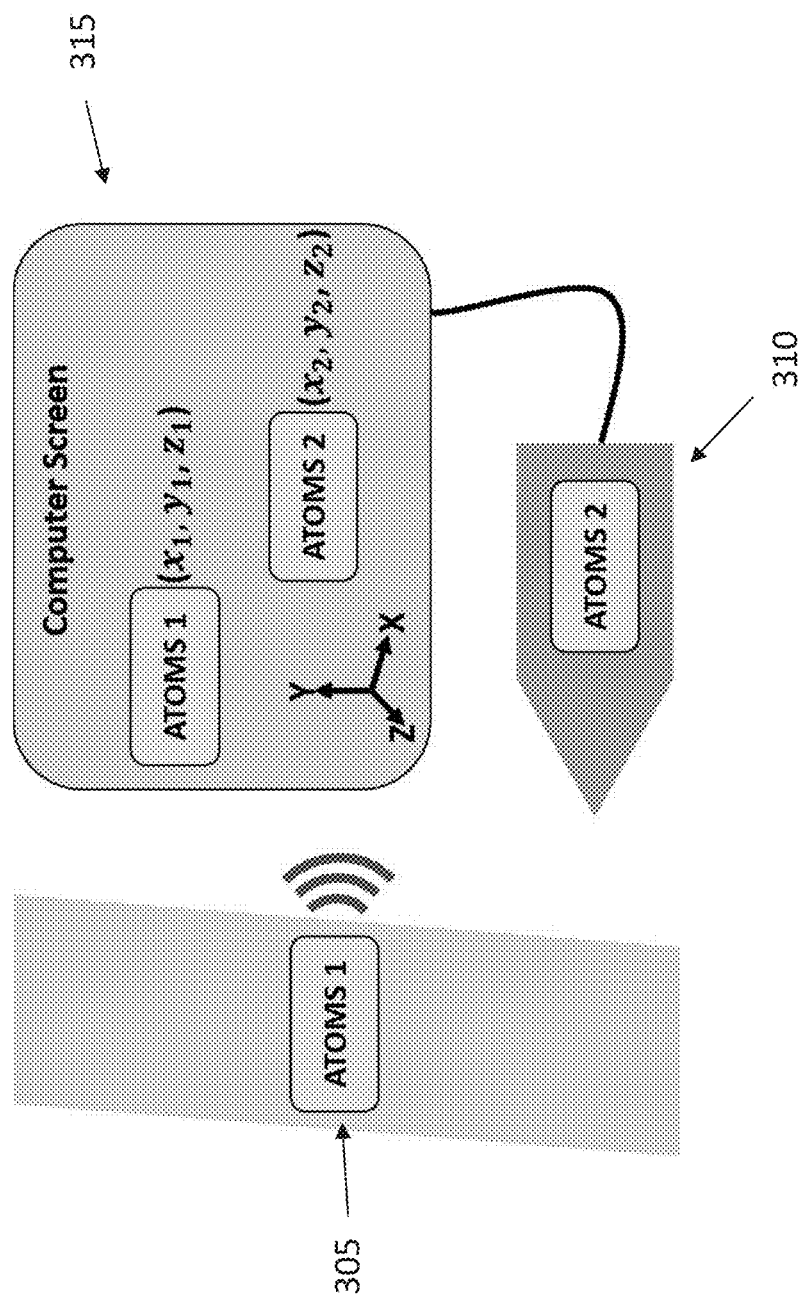
FIG. 3 illustrates a schematic of ATOMS positioning.
Figure 28:
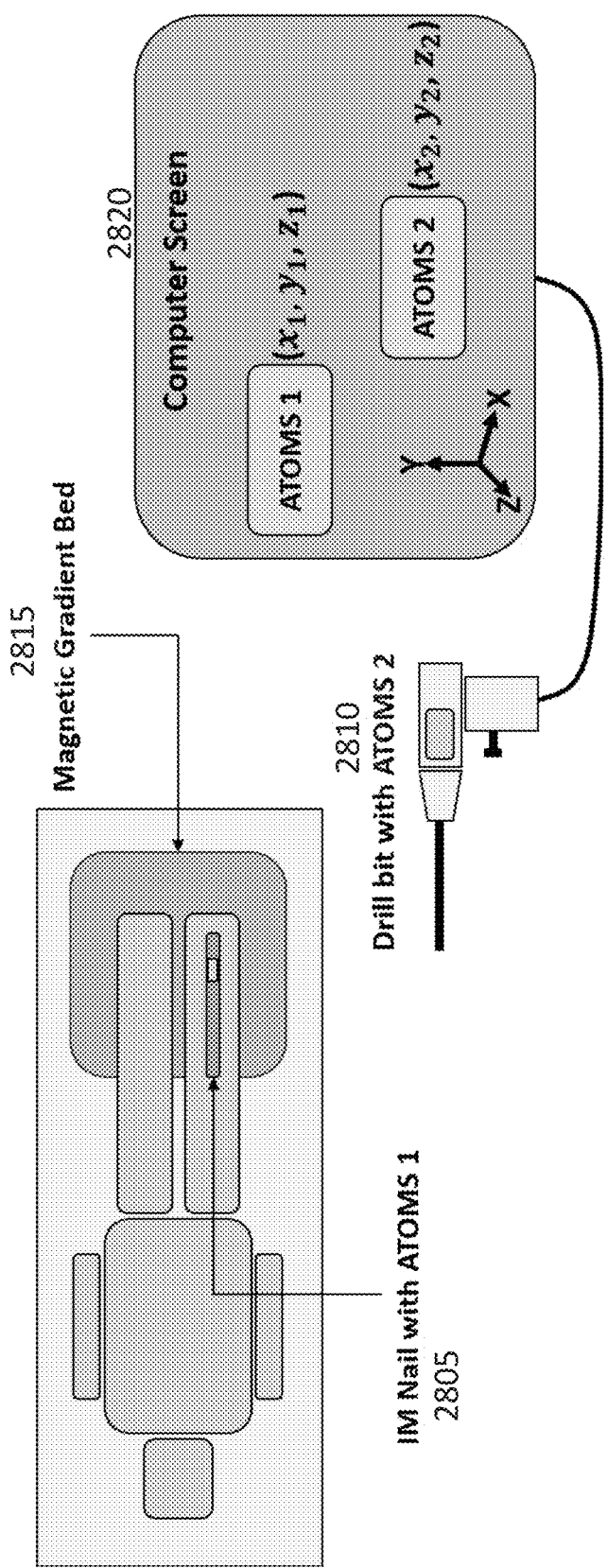
FIG. 28 shows a system overview.

FIG. 3 shows an overview with two ATOMS (305,310), a drill and the computer screen to be used during the operation; ATOMS 1 (305) is located inside the human body, and ATOMS 2 (310) is on the drill. The 3D location of both is displayed on the computer screen (315). FIG. 28 illustrates a system overview comprising a nail (2805), a magnetic gradient bed (2815), a drill bit (2810), and a computer display (2820).

An ATOMS sensor can comprise the following components: a 3D magnetic Hall sensor; an integrated circuit (IC) chip; a power source; and a radiofrequency (RC) coil. The 3D magnetic Hall sensor is used to sense the magnetic field at the location of the ATOMS. Positioning works by having unique field values at all the points of interest, to allow a one-to-one mapping between positions and magnetic field values. The sensor output is a digital field value which is given to the IC chip for further processing. In order to have good spatial resolution, a high resolution 3D magnetic hall sensor is used, so that the required magnetic field gradients remain within an acceptable range.

The IC chip includes the circuitry for transmission of data values through a chosen standard for wireless communication. A challenge here is to ensure that communication is done in a power efficient way. Therefore, data telemetry can be carried out through backscattering, a technology for wireless data communication in low power applications. The chip also carries out timing generation, allowing data measurements in a time multiplexed fashion, to not incur unnecessary power losses. Time multiplexing requires wake up and sleep signals for the various components of ATOMS, which are generated by the IC chip.

Figure 5:
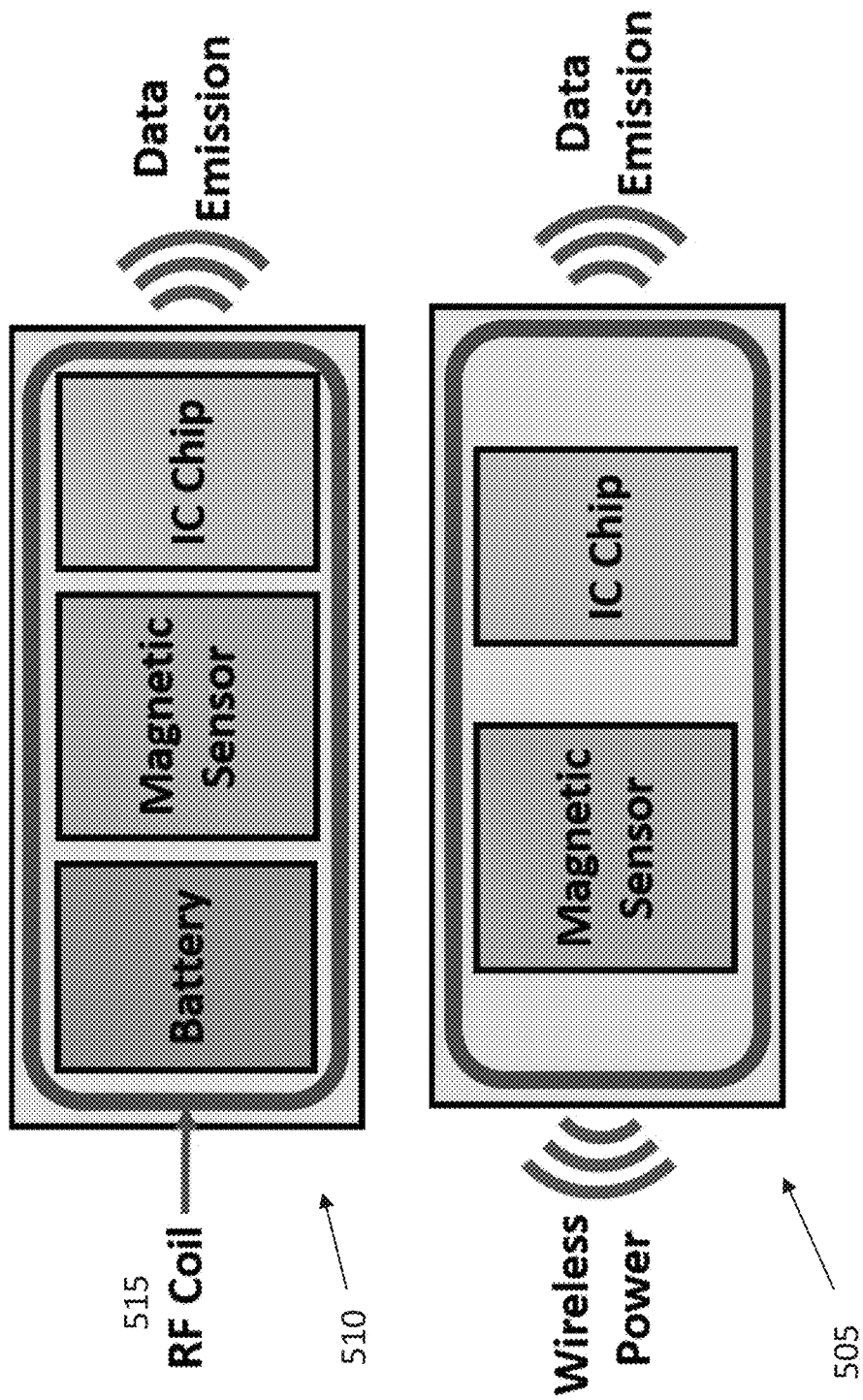
FIG. 5 illustrates two power delivery arrangements.

The power source can employ wireless power transfer as well as battery-based solutions, as illustrated in FIG. 5. In the example of FIG. 5, a RF coil (515) is present around a perimeter of the ATOMS, with the battery, magnetic sensor, and IC chip in the internal area to reduce the overall volume requirements. Wireless power transfer for a biological tissue depth of 10 cm (a typical IM nail location) entails large tissue absorption. Therefore, the battery based power supply can be considered as an alternative solution.

An RF coil can be used for wireless communication through backscattering. The RF coil on ATOMS can sense an RF signal and modulate it accordingly, to convey the field value data to an external receiver. The RF coil is also needed when using wireless power transfer to ATOMS. In some embodiments, the wireless power transfer (WPT) is turned off during data transmission.

In some embodiments, the 3D magnetic sensor has a high magnetic field resolution, for example of 1.1 µT or better; a low power consumption, e.g. an average of 10 µW or less; a high field measurement dynamic range in the three axes components of the fields Bx, By and Bz (e.g. ±35 mT); a 16-bit data resolution for the in-built ADC for each measurement direction; a low leakage current (e.g. 2 nA); and selectable sensor measurement range and sensitivity setting. In some embodiments, the sensor may have a $I^2C$ bus interface with 4-wire SPI. For example, a commercially available sensor with the above characteristics in a 16-pin QFN package has dimensions of 3.0 mm×3. mm×0.75 mm. On-chip 3D magnetic sensors can also be used for this application as this arrangement can make the system more compact. Important characteristics are the sensor power, which needs to be low, and the sensor resolution, which should be high enough to allow working with relatively low magnetic field gradients.

The fundamental relationship between the spatial resolution ($\Delta x$) of the sensor and the corresponding magnetic field gradient ($G_x$) required to obtain this resolution, given the minimum field value the sensor can measure accurately ($\Delta B_{min}$), is given by Eq. (1):

$$\Delta x = (\Delta B_{min})/G_x \quad (1)$$

Figure 6:
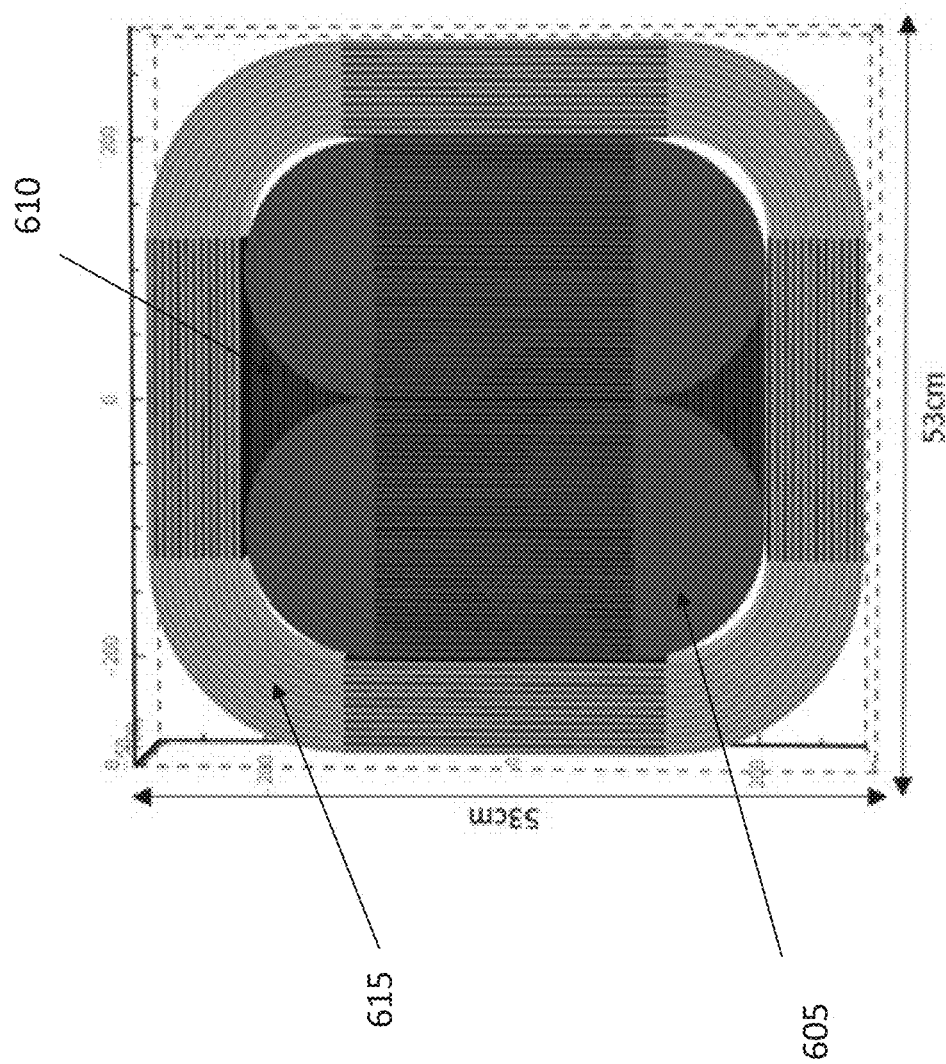
FIGS. 6-8 illustrate a set up for the magnetic gradient coils.
Figure 7:
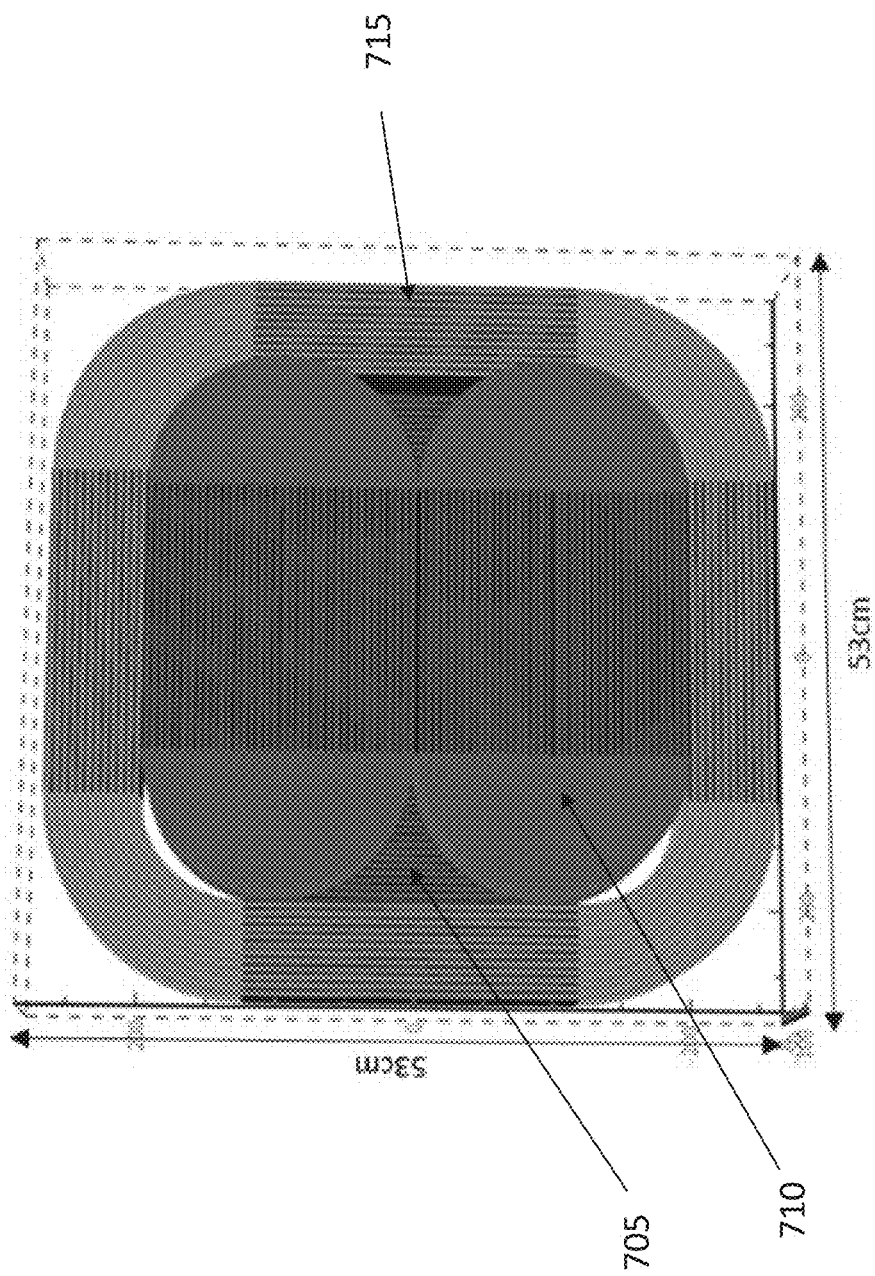
Figure 8:
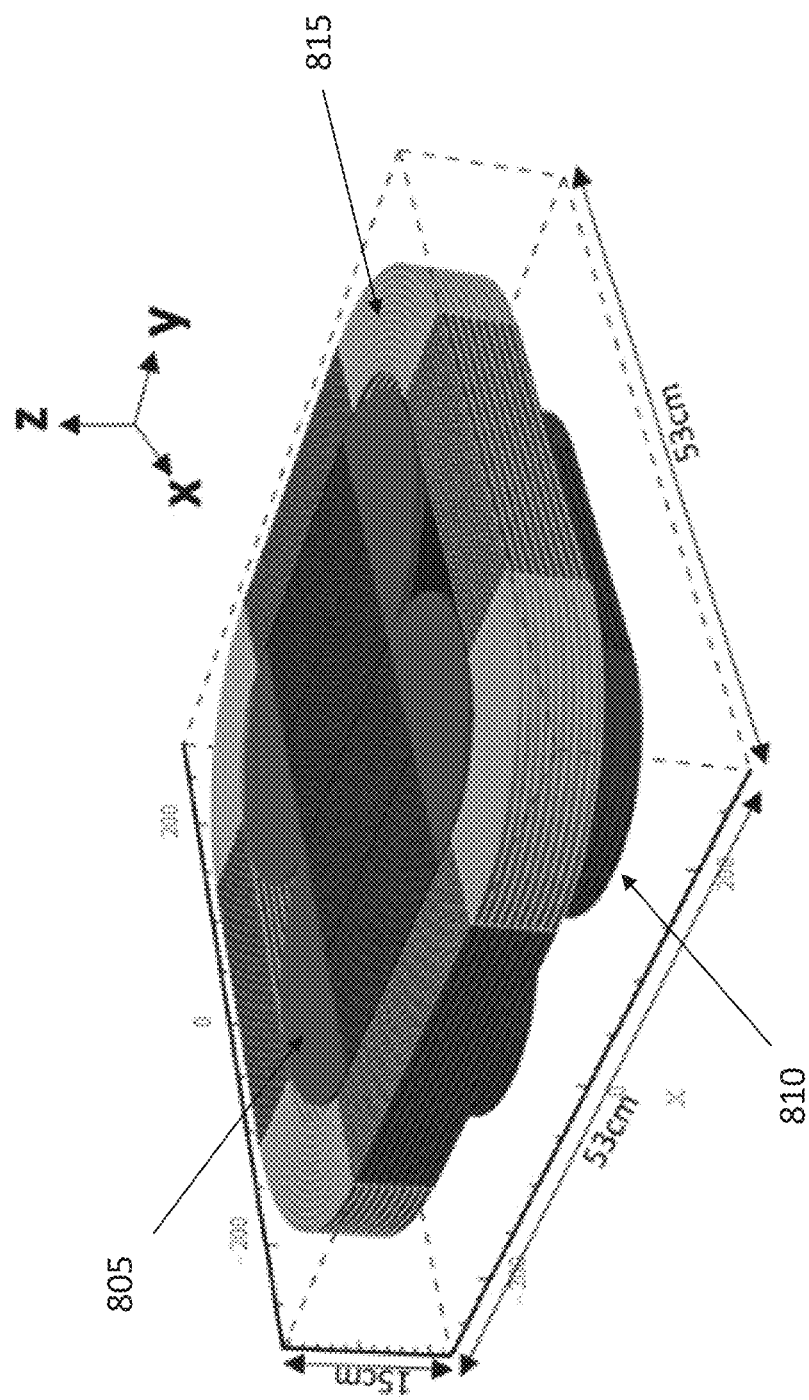

In Eq. (1), $\Delta B_{min}$ is dictated by the specifications of the magnetic sensor and the resolution of the ADC used. In some embodiments, for the sensor having the above characteristics, it ranges from 1.1 µT to 3.1 µT or better. In order to obtain a $\Delta x$ better than 100 µm, the sensor requires a magnetic field gradient of 30 mT/m for the lowest sensor resolution. In order to obtain the required field gradients, a specific setup of gradient coils can be used, as shown in FIGS. 6-8. FIG. 6 illustrates a top view of the coils, while FIG. 7 illustrates a bottom view, and FIG. 8 a side view. FIG. 6 illustrates x axis coils (605); y axis coils (610); z axis coils (615). FIG. 7 illustrates x axis coils (705); y axis coils (710); z axis coils (715). FIG. 8 illustrates x axis coils (805); y axis coils (810); z axis coils (815). As visible in FIG. 8, they coils are in a plane parallel to that of the x coils, and are oriented rotated by 90° relative to the x coils.

Figure 9:
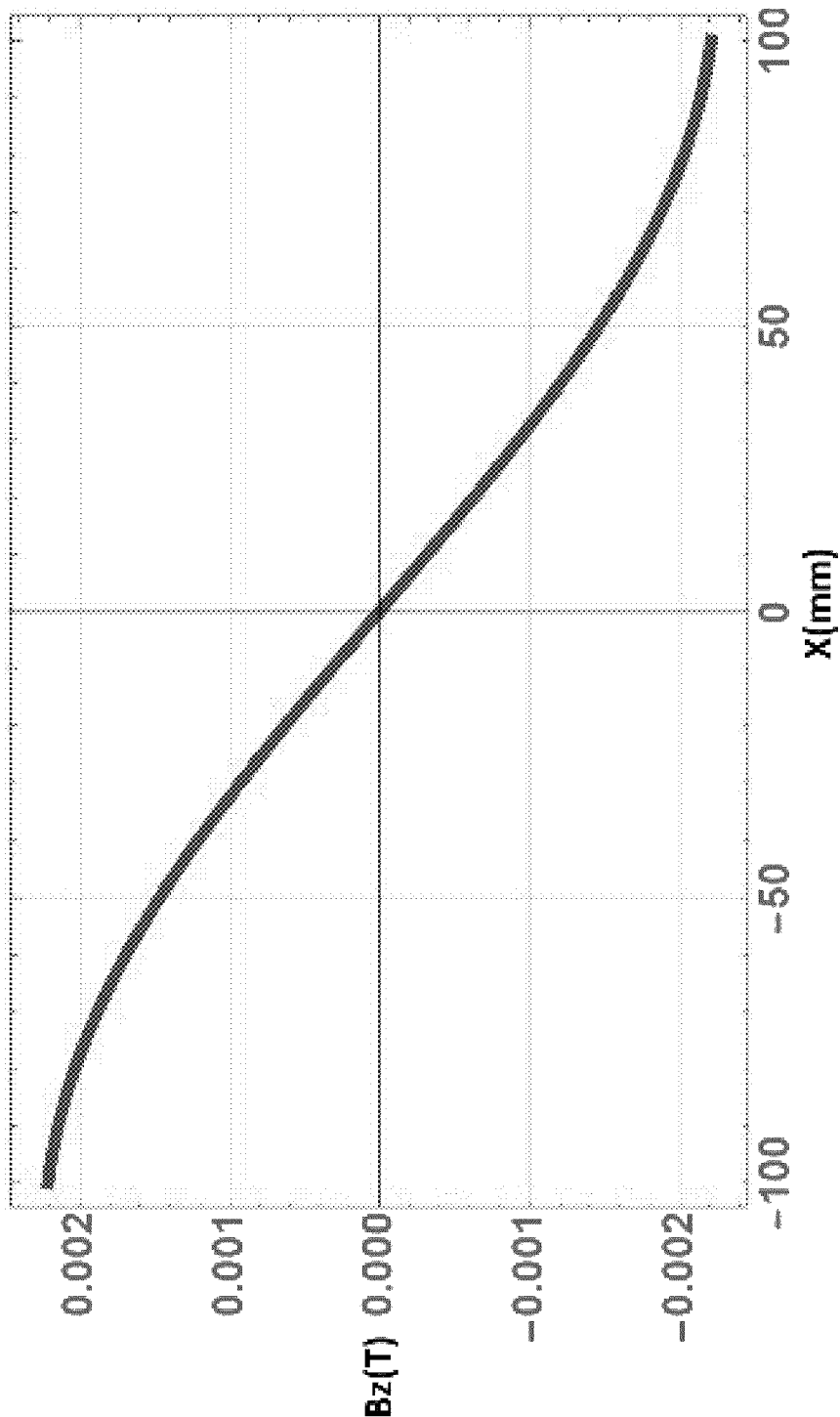
FIGS. 9-11 illustrate magnetic field gradients.
Figure 10:
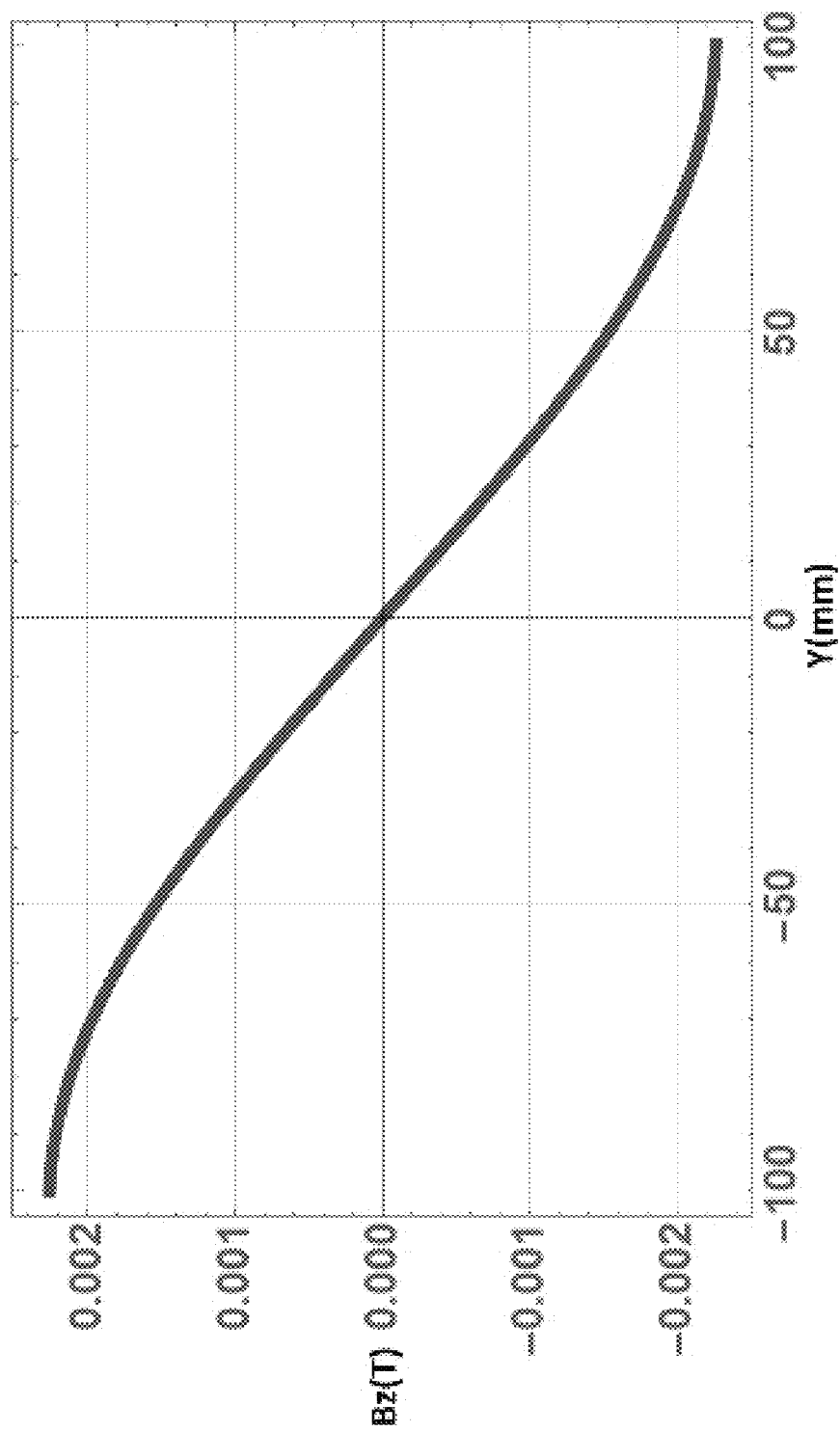
Figure 11:
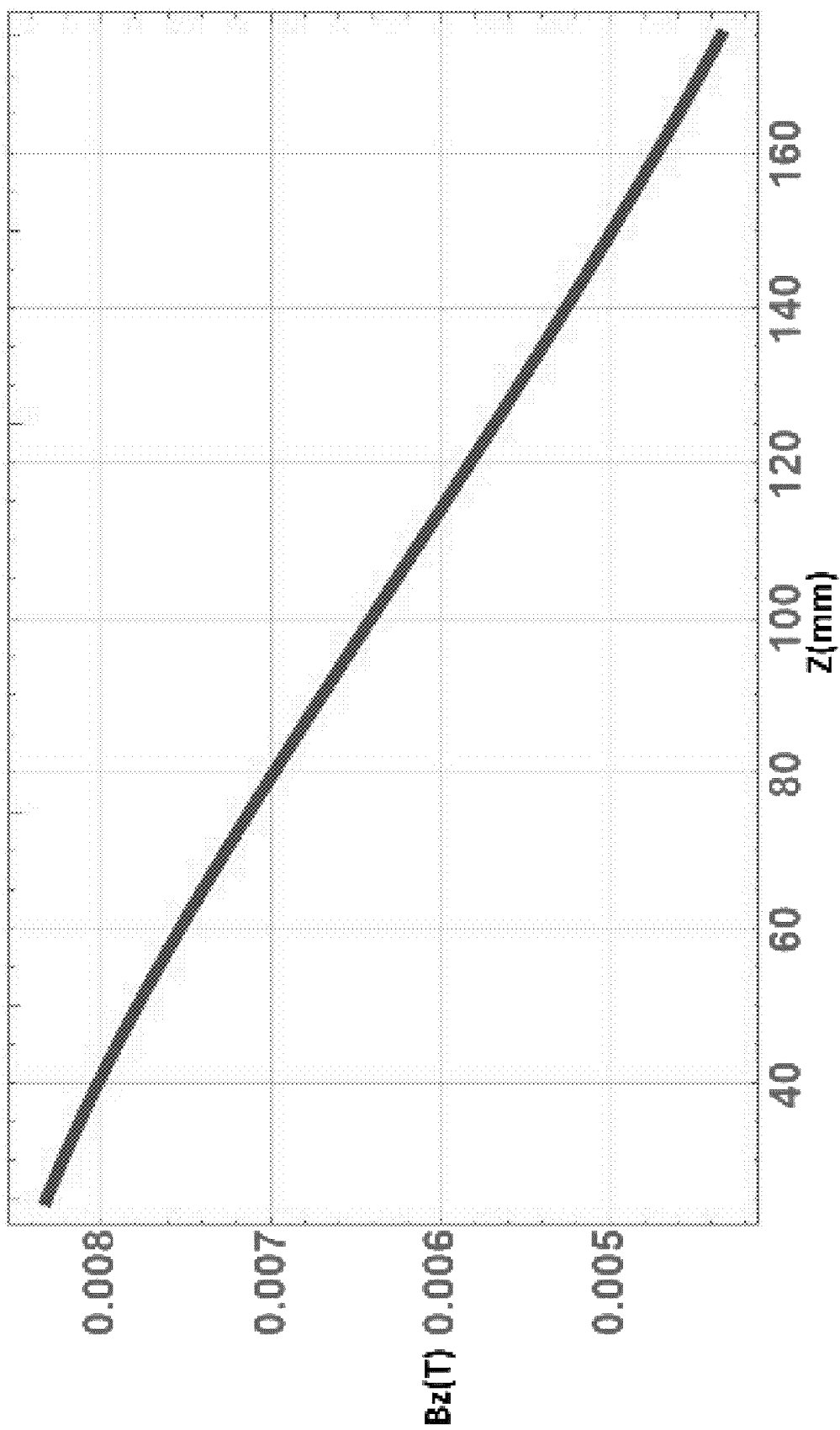

With reference to FIGS. 6-8, the x axis coils carry current in opposite directions with respect to each other, thus creating a magnetic field gradient along the x direction for the z axis magnetic field component. Similarly, the two y axis coils lying underneath the x axis coils carry opposite currents with respect to each other, which gives rise to a gradient along y direction for the z axis magnetic field component. The gradient along the z direction for the z axis magnetic field component is created by the set of z axis coils, all carrying current in the same direction. The magnitude of the axial magnetic field for the z axis coils decays along the z axis, thus creating a gradient along the z direction. The generated field gradients are shown in FIGS. 9-11. FIG. 9 illustrates a magnetic field gradient of 30 mT/m in the x direction. FIG. 10 illustrates a magnetic field gradient in the y direction. FIG. 11 illustrates a magnetic field gradient in the z direction. The current densities used to generate these gradient fields are: 0.54 A/mm² for the x coils, 0.62 A/mm² for the y coils, and 1.1 A/mm² for the z coils.

As observed in FIGS. 9-10, the gradients in the x and y directions attain their maximum values at x=0 and y=0, respectively. FIG. 11 shows that the maximum gradient in the z direction occurs at 10 cm, which also lies at the center of the operational range. This design allows the highest gradient regions to occur at the center of the operational range, corresponding to the location of the hole on the IM nail inside the bone. The monotonic nature of the magnetic fields ensures a unique mapping of all points in space to the corresponding magnetic field values.

The gradient fields have a range large enough to accommodate both of the ATOMS devices: the device on the IM nail and the device on the drill. The overlap is especially useful in the initial phase of the surgical procedure, when the ATOMS on the drill is far from the intended final location. As seen in FIGS. 9-11, the designed coil setup allows a working range of 15 cm-20 cm, which is more than sufficient for a typical IM nailing surgery. As the drill comes closer to the desired final location, the resolution improves. The coils generating the magnetic field can be placed, for example, under the patient's leg in an operating theater bed, if the broken bone is within the leg.

Since power delivery to ATOMS can be challenging, especially if performed wirelessly, it is useful to reduce power consumption. Therefore, judicious use of power is useful at every step, a major part of which can be achieved by turning on the individual components of ATOMS only when needed, and sending them to a dormant or sleep mode when not in use. Therefore, a time multiplexed approach for the complete system is useful in order to reduce the total power required by ATOMS.

Figure 12:
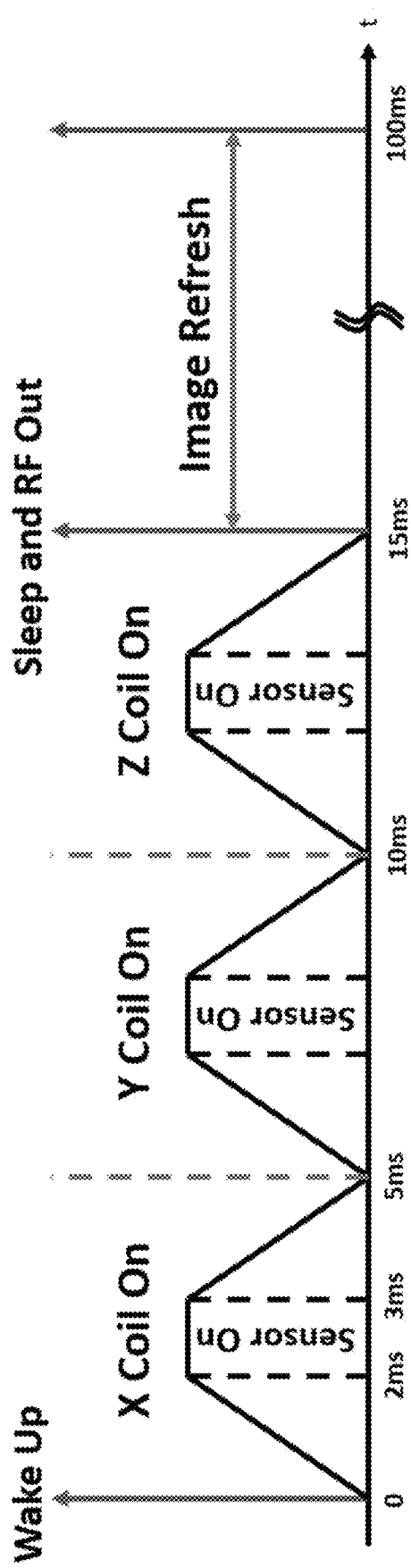
FIG. 12 illustrates time multiplexing.

The sequence of time-multiplexed measurements of the magnetic field gradients in each direction is shown in FIG. 12. Only the x coils are switched on during the x phase, and similarly for the y and z phases. First, a wake up command is sent to bring the system out of sleep mode. Then, the x gradient coils are turned on and allowed to reach a steady state value in about 2 ms (ramp-up time due to current switching in coils). Following this step, the field measurement takes place in the next 1 ms, and then the x gradient coils are turned off. The switching off phase takes another 2 ms, thus making the whole step 5 ms long. The same set of events is repeated for the y and z gradient measurements.

The 1 ms time window required to measure the field gradient in any given direction is dictated by the sensor used for magnetic field measurements. The reported time needed to make an accurate field measurement by the sensor described above is about 1 ms, thus requiring the gradients to be stable for at least that much time. This also implies that the sensor has to be turned on only for the desired 1 ms time window for the x phase, and then subsequently for the y and the z phases. Therefore, the total on time for the sensor is 3 ms in a 100 ms time frame. After all three measurements corresponding to x, y and z are made, the sensor and the coils are turned off for the next 85 ms through a sleep command. The person of ordinary skill in the art will understand that the above parameter values are exemplary, and if using a different sensor having different characteristics, a different measurement time would be employed.

Following the measurements, ATOMS performs data processing and field value transmission through an RF signal. This step provides a visual feedback to the surgeon monitoring the updated computer screen (image refresh phase) and gives the surgeon enough time for maneuvering the drill to the updated location. To position the implanted ATOMS with respect to a reference, a second ATOMS is located on the drill, the position of which is also constantly displayed on the computer screen.

The complete process makes the duty cycle for the gradient switching to be 5% for each of the coils, including the switching time. In some embodiments, 10 such measurements can be carried out per second. This reduces the time to locate the hole in IM nailing surgery to only a couple of seconds, which is a major advantage over the existing solutions which take a couple of minutes along with continuous fluoroscopy to locate the hole in the IM nail.

In some embodiments, back scattering is used for wirelessly sending the measured field data to the external device for position tracking. As known to the person of ordinary skill in the art, this form of data transmission is particularly useful for low power applications. The two main components of a backscatter communication system are the backscatter transmitter and a reader. The reader comprises a radio frequency source along with a backscatter receiver. The RF signal is generated by the reader, while the backscatter transmitter modulates and reflects the signal to transmit its data to the backscatter receiver. The modulation produces a digital signal with a varying pulse width, based on the change in effective impedance of the RF coil in response to the impinging RF pulse. In some embodiments, the RF source for ATOMS can operate at 13.56 MHz, which lies in the ISM band for biomedical implants. The tissue absorption at this frequency is much lower compared to the higher frequencies normally used for such applications. The Q factor of the RF coil, which determines the efficiency of the device, is also high at this frequency.

For the ATOMS device attached to the drill, wireless power transfer and data-backscattering can be completely eliminated, in some embodiments, by having wired connectivity to the device. Since the drill bit is anyway tethered to a cable, it can be relatively easier to have wired connections for power transfer and data communication to the ATOMS device instead of performing the same over wireless medium. Another possibility is to perform optical tracking of the drill instead of having an ATOMS device for its positioning. The use of infrared based light emitting diodes is known to the person of ordinary skill in the art, for optical tracking of surgical tools. Gyroscope assisted tracking and passive markers like retro-reflective spheres, disks are also potential candidates for the same.

As ATOMS can be implanted inside human body, it is essential to hermetically seal the device using a bio-compatible plastic. In some embodiments, encapsulation is carried out with polyetheretherketone (PEEK). PEEK has widespread use in prostheses, dental products and replacements for metal implants inside human body.

For the timing sequence of FIG. 12, an on-chip clock synchronizes the time for the sensor and the gradient coils. This synchronization can be achieved by implementing an ultra low power relaxation oscillator which consumes a total power of less than 1 nW, an extremely negligible amount compared to the 10 µW of power consumed by the 3D magnetic sensor. The magnetic field data obtained from the sensor is used to modulate the RF signal coming from the backscatter reader. The modulated signal is read by the backscatter receiver located externally. The modulation process is not power hungry and therefore the major power consumption of ATOMS comes from the 3D magnetic sensor.

By adopting a time multiplexed strategy for the field measurement in the x, y and z axes, the average power consumed by the magnetic sensor is 0.3 µW as it remains on only for 3 ms out of 100 ms. The other circuit blocks, as described above in the present disclosure, consume negligible power compared to the sensor. Therefore, the average power consumption of ATOMS can be approximately less than 1 µW. For such a low power requirement, battery based solutions can be used, as they can easily provide the required power for the duration of an IM nailing operation. For example, a rechargeable solid state bare die can be used. It has a capacity of 5 µAh which is more than sufficient for the implanted ATOMS for a couple of hours, the typical duration of an IM nailing operation. The battery footprint, for example, can be 1.7 mm×2.25 mm×0.2 mm, which is well within the dimensions of ATOMS and can be easily incorporated into the complete system.

For the various current densities used to create magnetic field gradients in all the three dimensions, the average heat loss from the coils is expected to be 8 W. For the given volume of the coils, this causes an increase in the coil temperature of less than 0.1° C., assuming copper metal is used for the coils. This negligible amount of heat relaxes the constraints on cooling mechanism, which reduces the overall complexity and cost of the system. The heating issue can be resolved by placing a cooling fan below the coil setup, and encapsulating the complete setup with a thermal insulator.

Figure 13:
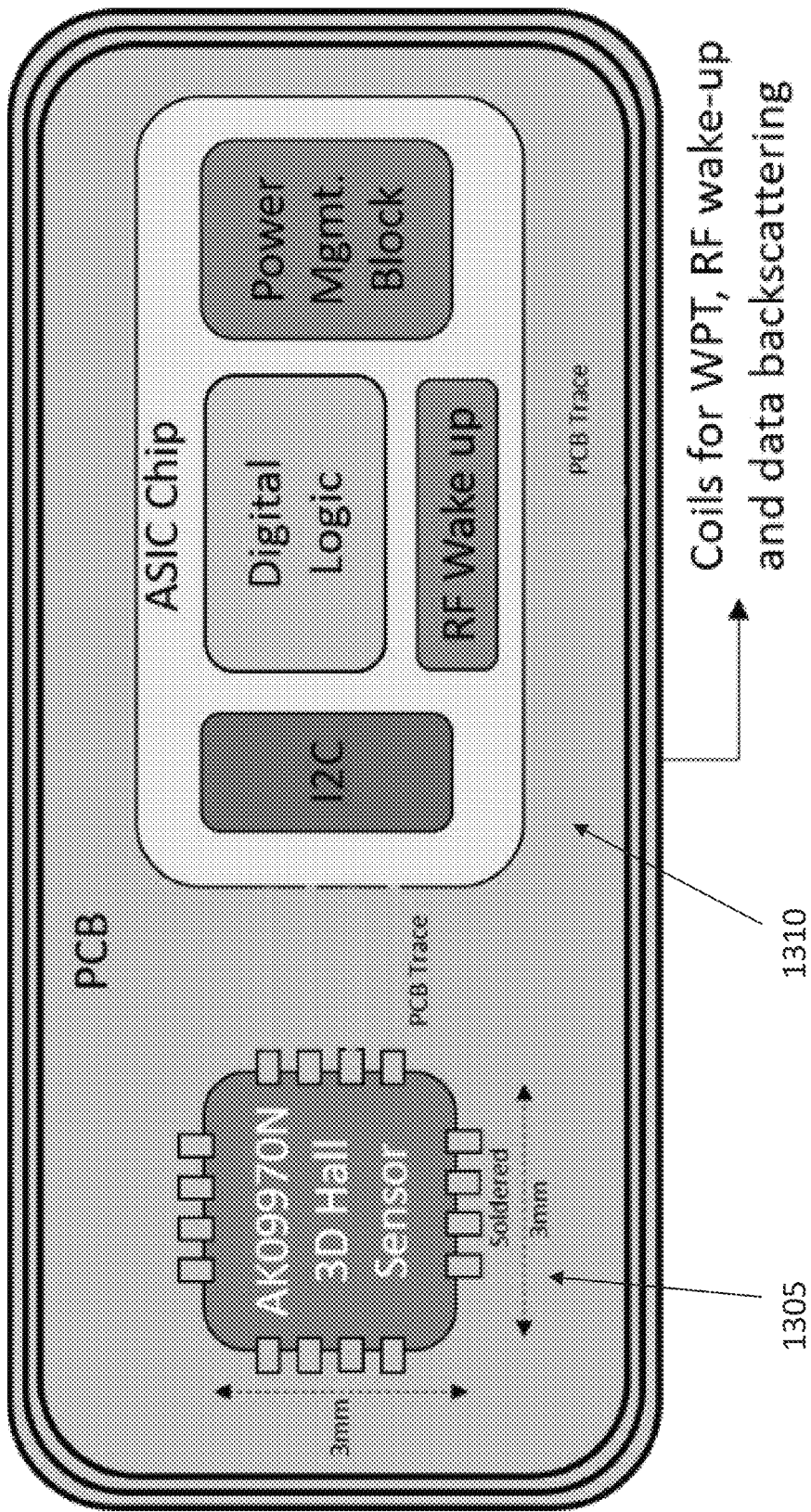
FIG. 13 illustrates an exemplary PCB with a Hall sensor.

FIG. 13 illustrates an exemplary PCB with a Hall sensor (1305), and an application specific integrated circuit (ASIC) chip (1310), comprising a power management block, and communication modules with the Hall sensor and wake up signals. The 3D magnetic Hall sensor, ASIC chip and the RF coils are all mounted on a printed circuit board (PCB) which is 10 mm by 5 mm (a typical implant size for ATOMS device). The sensor is soldered on the PCB and then connected to the ASIC through copper traces. The ASIC itself is wire-bonded to the PCB using very fine strands of gold wire. The RF coils are mounted all around the PCB and then connected to the ASIC through copper traces. The back of the PCB contains storage capacitors which store power received from the coils. These are essential because the most power hungry phenomena during the ATOMS device operation is magnetic field measurement by the sensor. This occurs for a very short time frame and the instantaneous RF power is insufficient to carry out a field measurement successfully. Hence, the storage capacitors store the power received from the RF coils which can then be used during the measurement phase. Enough time is provided between consecutive measurements for the storage capacitors to re-charge to their required values. Table 1 lists some exemplary specifications for individual components of a sensor.

TABLE 1

| | |
|---|---|
| Localization resolution | 100 µm, 3D |
| Magnetic sensor resolution | 1.1 µT/LSB (16 bit output) |
| Magnetic sensor dimensions | 3 mm × 3 mm × 0.75 mm |
| Battery capacity | 5 µAh |
| Battery dimensions | 1.7 mm × 2.25 mm × 0.2 mm |
| ATOMS dimensions | 10 mm × 5 mm |
| ATOMS avg. power consumption | 1 µW |
| Encapsulating bioplastic | PEEK |
| Image refresh rate | 10 times per second |
| RF frequency for data transmission | 13.56 MHz |
| Supported range above coil bed | 15 cm-20 cm |
| Total navigation time | 2 hrs |

Figure 14:
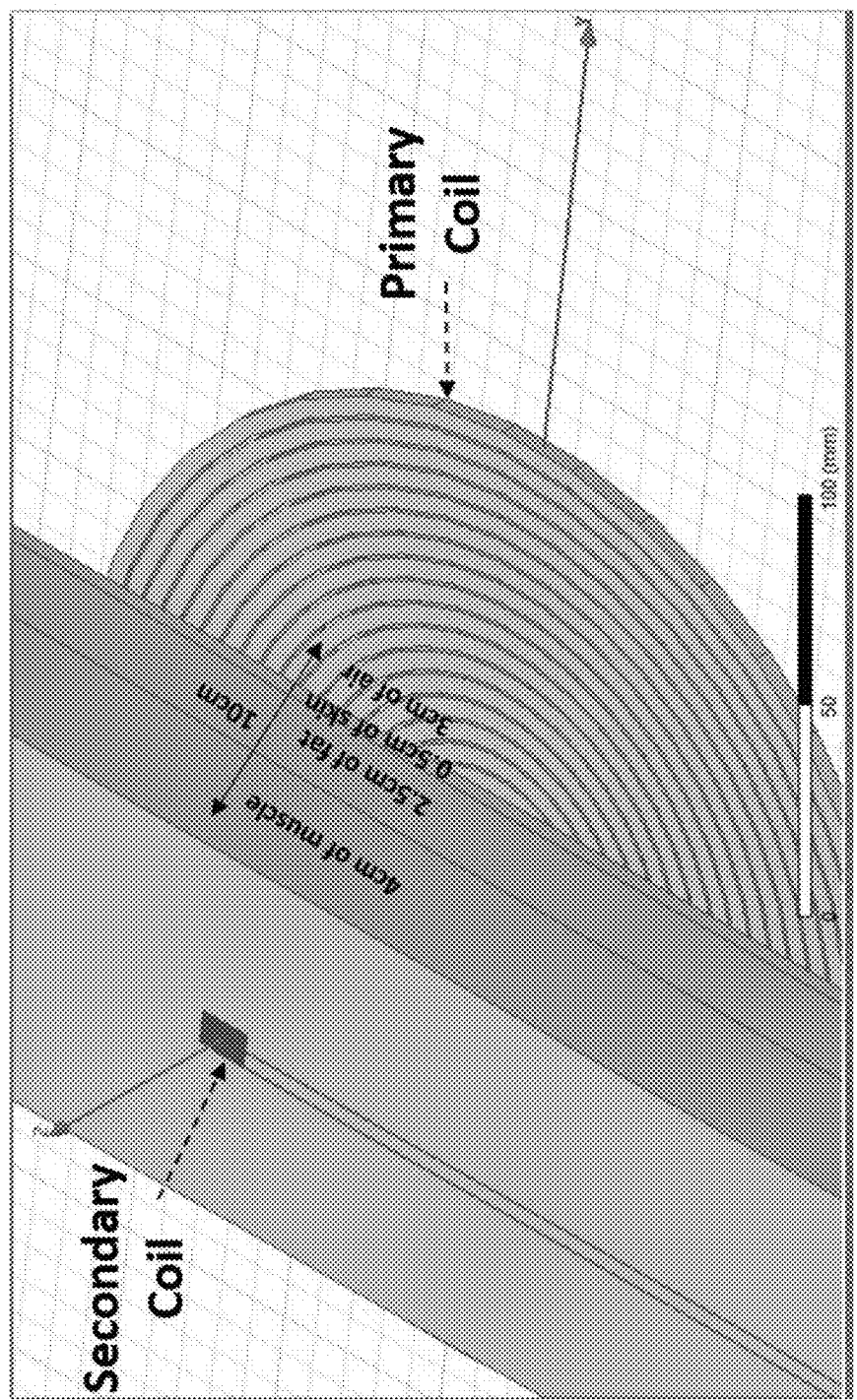
FIG. 14 illustrates a simulation setup.

It is possible to model the RF coils to calculate the inductances of the primary and secondary side coils in the presence of human tissue. The human tissue can be modelled as a composition of muscle, fat and skin having a depth of 4 cm, 2.5 cm and 0.5 cm respectively. The primary coil in this simulation is kept 3 cm above the skin, giving a total separation of 10 cm between the coils. The complete simulation setup is shown in FIG. 14 and the extracted parameters are listed in Table 2.

As seen from Table 2, the coupling coefficient between the coils in presence of human tissue is 0.001624. This value can provide a few milliWatts of power at the implant depth. In this example, the power consumption of the sensor can be restricted to be 1 mW for the complete ATOMS device, including the magnetic field sensor.

Figure 15:
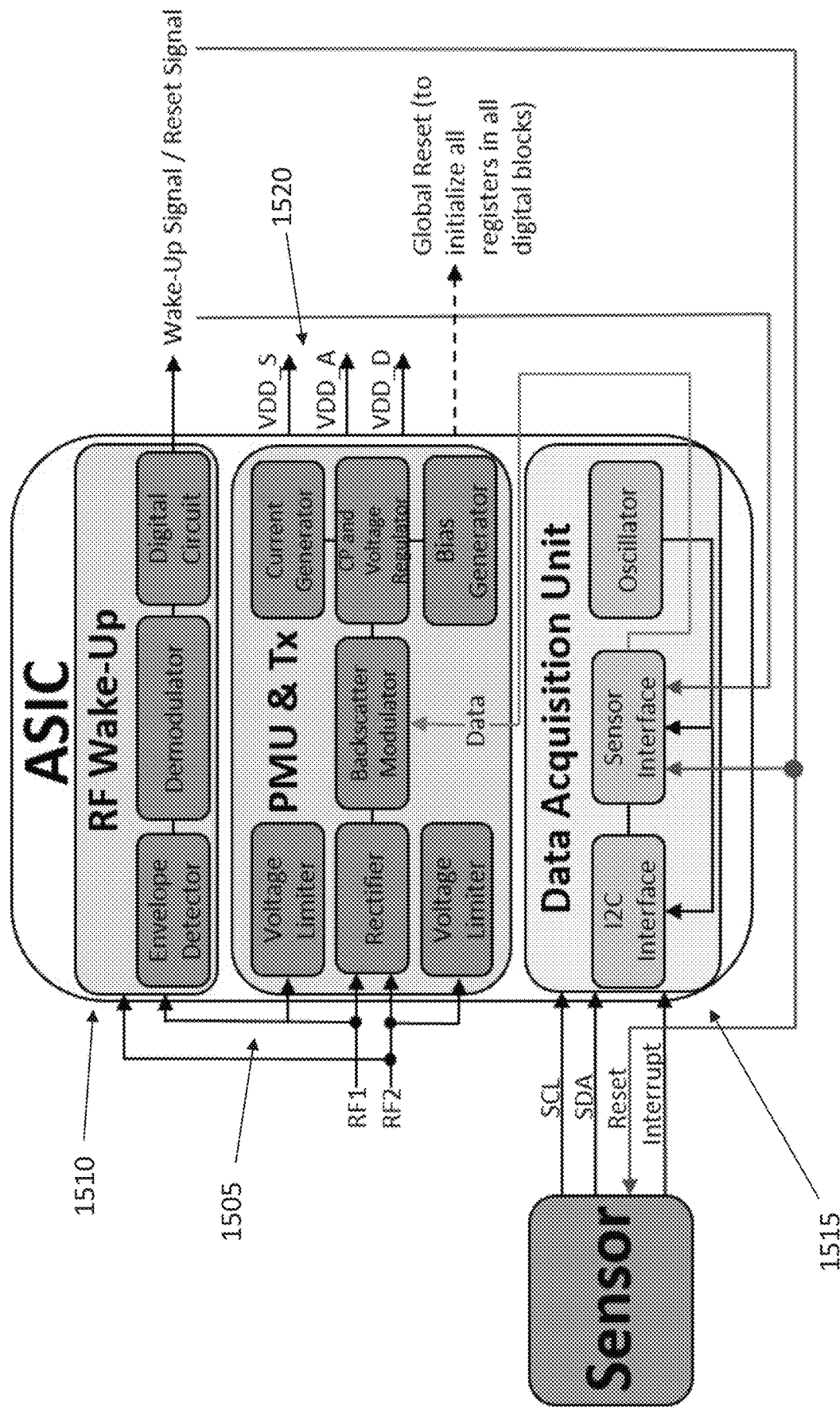
FIGS. 15-16 illustrate an exemplary ASIC implementation.

In some embodiments, the ASIC chip discussed above is responsible for (a) power reception and distribution; (b) data collection, processing and emission; and (c) wake-up when triggered by externally transmitted RF signal. To carry out these three tasks, the ASIC chip has three major components as described in the following, and as illustrated in FIG. 15: a power management unit, an RF wake up module, and a data acquisition unit.

The power management unit (PMU) handles the power requirements. The RF power, for example sent wirelessly at 13.56 MHz, is converted into DC power using a rectifier, which forms the front-end of the PMU block. Since the power received depends on the distance and alignment between the primary and secondary coils, it is expected to vary during the IM nailing operation. This power variation can lead to much higher voltage being induced at the secondary coil when the separation decreases, which in turn can damage the whole circuitry. In order to keep this induced in safe range, voltage limiters are used in the PMU.

The rectified voltage (typically 0.6 V) may need to be boosted up because the subsequent circuit blocks and the sensor usually need higher voltages to operate correctly. The voltage boost can be achieved by a charge pump circuit, which can, for example, boost the rectified voltage by a factor of 4. In some embodiments, the charge pump output voltage is then fed to regulators to produce three stable and regulated voltages (1520): (a) VDD_S is 2.4 V and is used as supply voltage for the sensor; (b) VDD_A is 1 V and is used as supply voltage for the analog circuit blocks of the ASIC; (c) VDD_D is 0.5 V and is used as supply voltage for the digital circuit blocks of the ASIC. To generate these supply voltages, other circuit blocks like bias voltage generators and current generators can be used. Table 2 lists coil parameters.

TABLE 2

| Parameter | Primary Coil | Secondary Coil |
| --- | --- | --- |
| Inductance | 43.457 µH | 11.797 µH |
| Quality Factor | 272K | 97.9 |
| Resistance | 13.6 mΩ | 10.266 Ω |
| Cross Section | 5 mm × 5 mm | 0.1 mm × 0.1 mm |
| Area | 24 cm diamater | 4.6 mm × 12 mm |
| Coupling Coefficient | 0.001624 | |

As mentioned above, the RF coils can serve two functions: WPT and data communication. The backscatter modulation switch, which connects the rectified voltage to charge pump, controls which of the two functions take place. In the normally ON mode, the switch allows the power to be transferred to the charge pump, and hence facilitates WPT. In the OFF mode, it disconnects the charge pump and modulates the RF signal on the coil, to backscatter the data to the external receiver.

For the wake-up signal, in some embodiments it is possible to transmit to the ASIC chip a 13.56 MHz RF signal, amplitude modulated with a 17 kHz pulse. To decode the wake-up signal from the RF carrier, an envelope detector first removes the 13.56 MHz frequency component from the signal, obtaining a 17 kHz pulse at its output. This pulse is further processed and demodulated in subsequent stages. Since reset signals are also transmitted to the ASIC in a similar fashion to the wake up pulse, a digital block is used to distinguish the wake up pulse from the reset signal. The output of the digital block is then used as a wake-up signal to initiate the magnetic field measurement by the sensor, or as a reset signal which resets the sensor interface block and the sensor.

The sensor is controlled by the data acquisition unit, which sends the commands needed for its operation. The sensor connects directly to the I2C interface on the ASIC, which follows the standard I2C protocol for data transfer, known to the person of ordinary skill in the art. This digital module provides the data and clock signals to the sensor and controls both of them as per the protocol. The 100 kHz I2C clock is generated on the ASIC using a ring-oscillator. The data line is bi-directional and is used for sending and receiving signals from the sensor. The sensor interface module in this unit controls the I2C interface module by activating it only when the wake-up signal is received. It also collects the data from the I2C interface module after a measurement is completed. This data is then used to control the backscatter switch, which modulates the RF signal across the coils in transmission phase.

Figure 16:
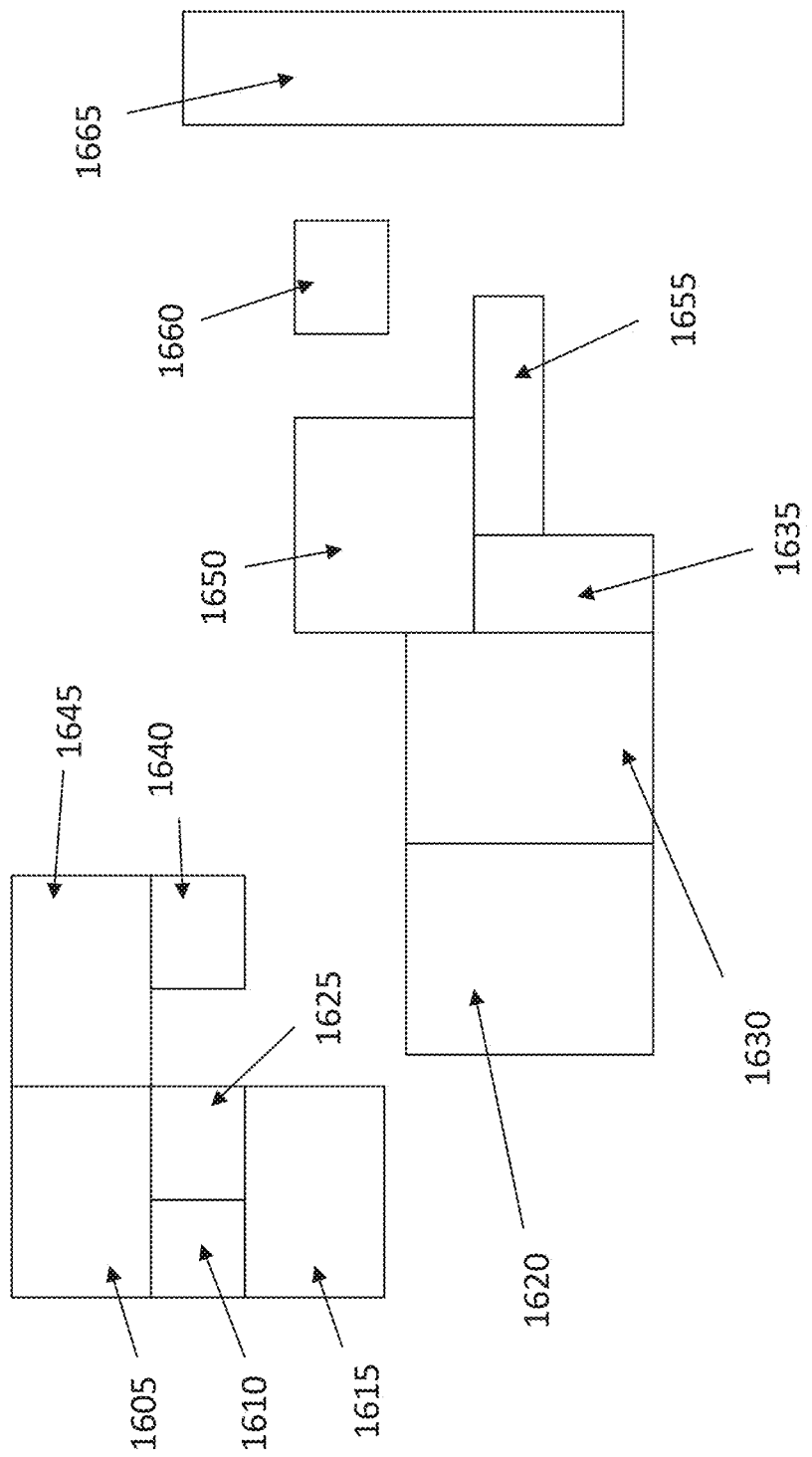

In some embodiments, a complete ASIC chip can be designed, with a 65 nanometer CMOS mixed signal, low power RF process. The complete layout of the ASIC chip, in this example, measures 1.5 mm by 1 mm and is shown in FIG. 16. FIG. 16 illustrates limiters (1605,1615); a rectifier (1610); a charge pump (1625); a current source (1645); an oscillator (1640); band gap reference (1620); voltage regulators (1630); RF wake up (1635); a regulator (1650); a digital processing block (1655); a I2C interface (1660); and a reference voltage generator (1665). The space surrounding the above components can also house noise cancellation and decoupling capacitors.

Figure 17:
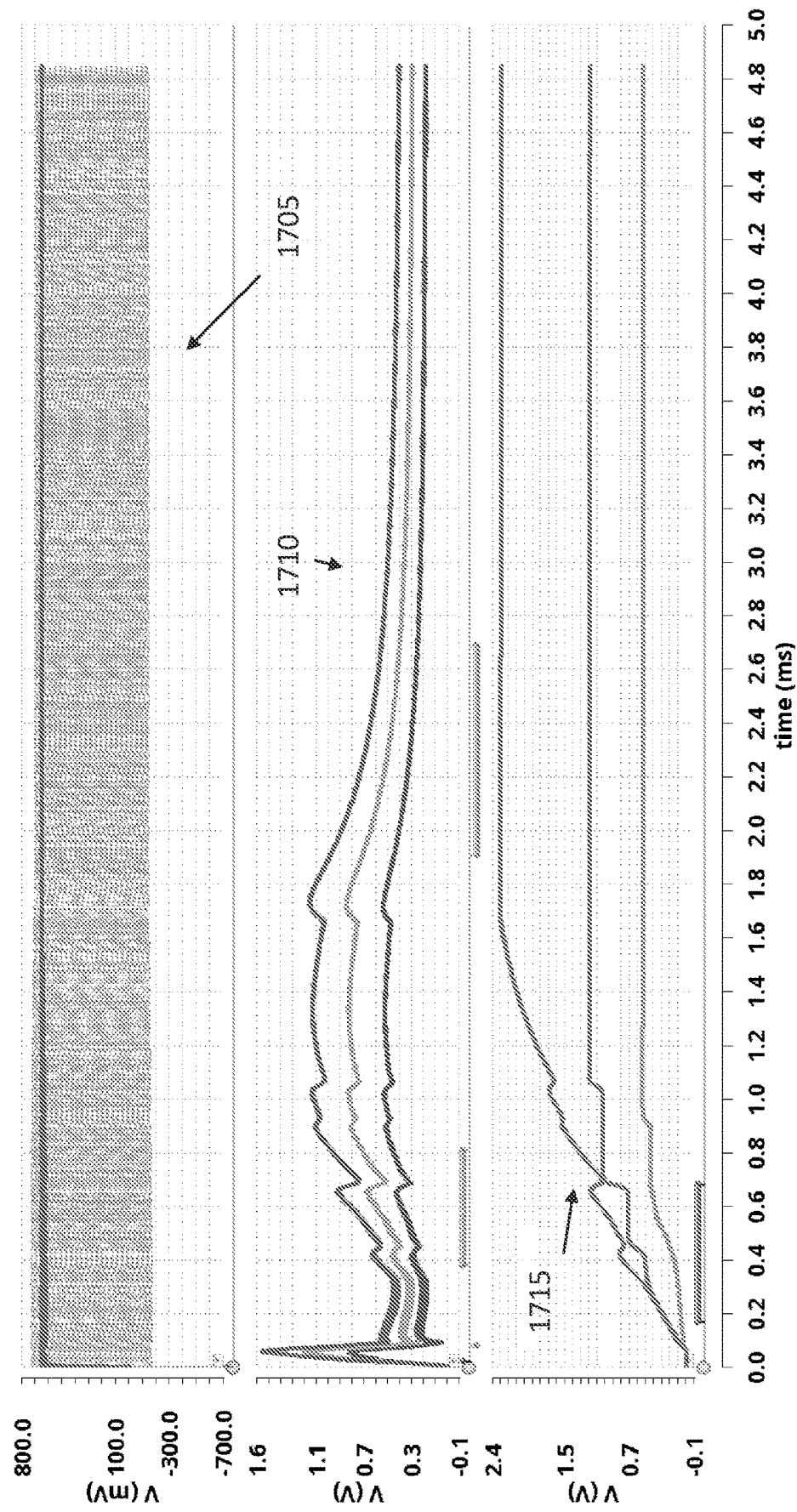
FIG. 17 shows the simulation results for the PMU unit.

FIG. 17 shows the simulation results for the PMU unit. The topmost waveforms (1705) are for the RF to DC power conversion by the rectifier which produces a stable DC voltage of 0.6 V from the alternating 13.56 MHz RF signal. The middle waveforms (1710) are for reference voltages, while curves (1715) are for the three supply voltages VDD_S, VDD_A and VDD_D.

Figure 18:
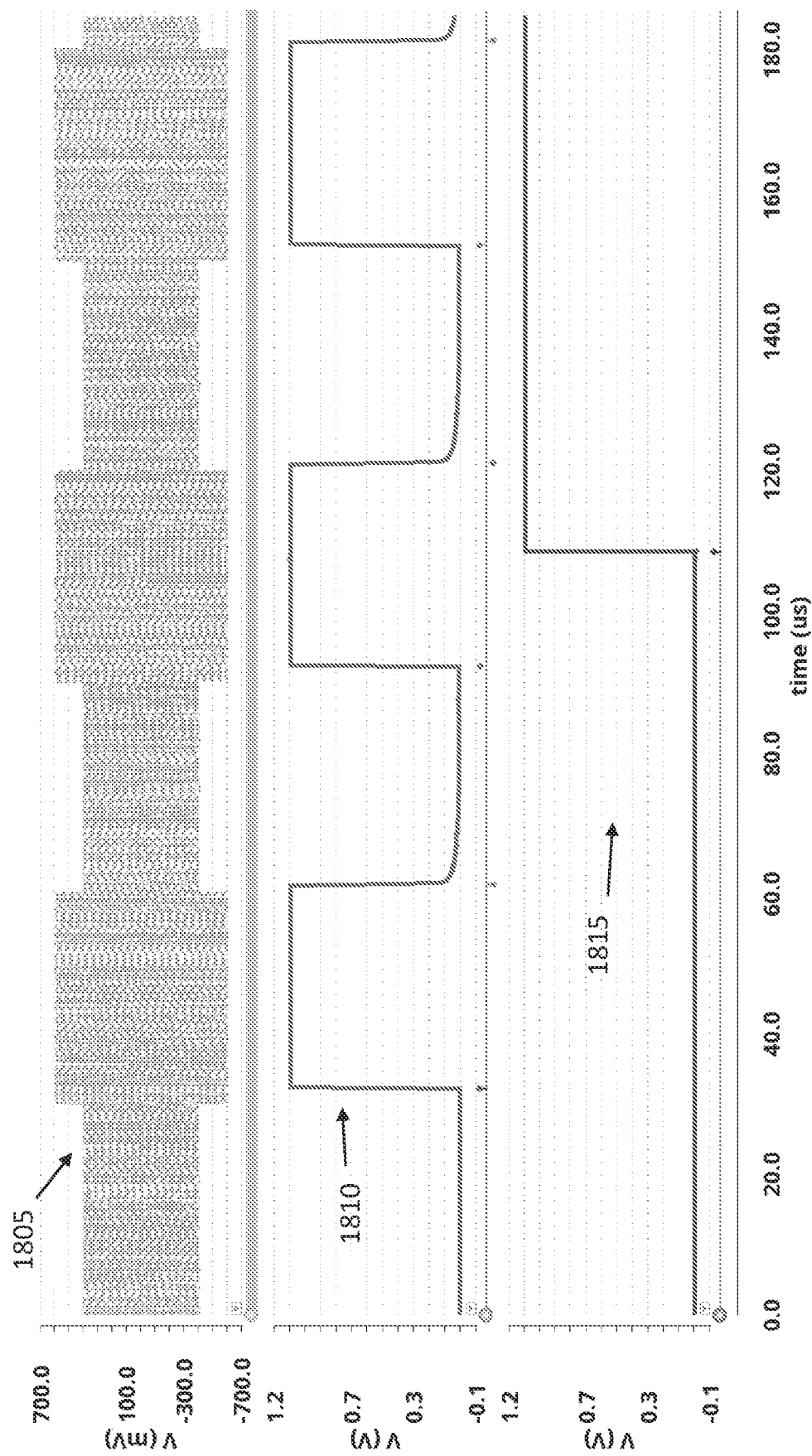
FIG. 18 shows the RF-wake-up block waveforms.

FIG. 18 shows the RF-wake-up block waveforms. The topmost waveform (1805) is for the amplitude modulated RF carrier (13.56 MHz) with a 17 kHz message signal on top of it. This has to be demodulated and processed to retrieve the 17 kHz message signal from the carrier, as shown in the middle waveform (1810). The last waveform (1815) is the output of the digital block and is generated after mapping the duration of the message signal to a fixed value. This is used as a wake-up signal for subsequent blocks.

Figure 19:
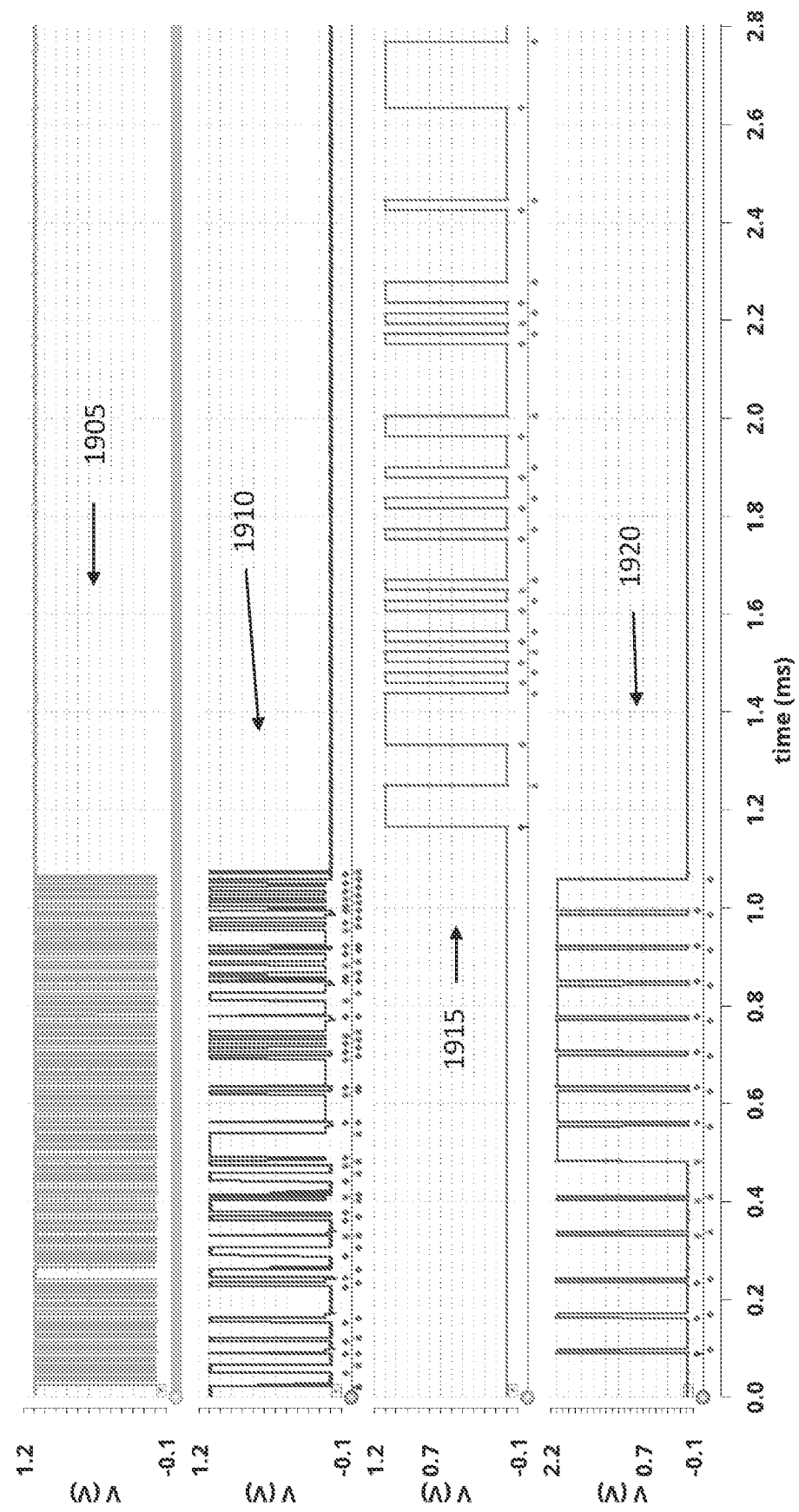
FIG. 19 shows the waveforms of the data acquisition unit.

FIG. 19 shows the waveforms of the data acquisition unit. The I2C interface block in this unit connects to the sensor through clock and data signals, shown as (1905) and (1910) respectively. The data collected is then transferred to the sensor interface block for processing. The processed data is illustrated as (1915). This is sent to the backscatter switch to modulate the RF signal's amplitude at a frequency of 50 kHz. The enable signal is illustrated as (1920) and controls the data flow direction between the sensor and the ASIC chip.

Figure 20:
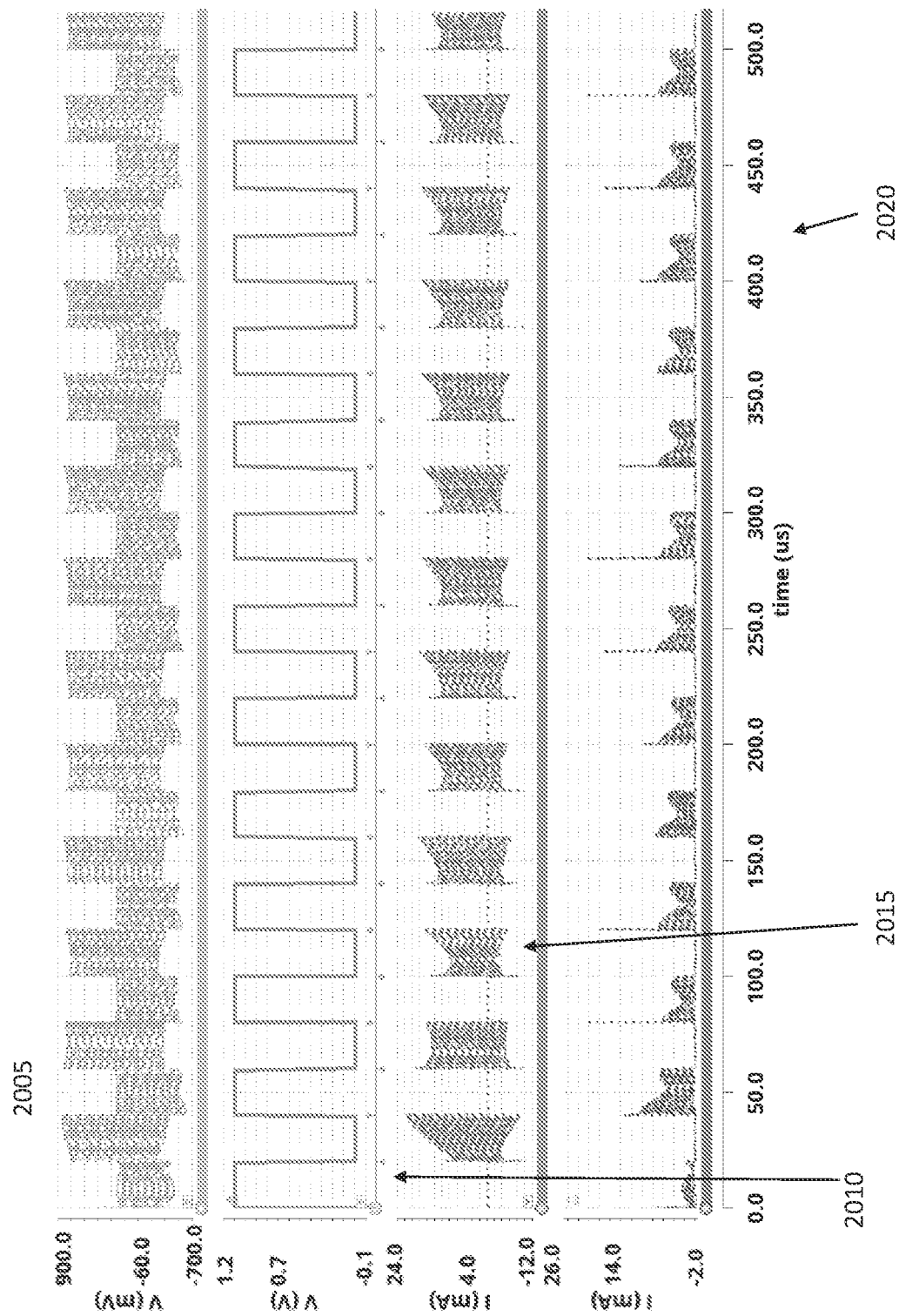
FIG. 20 shows the backscatter modulation waveforms.

FIG. 20 shows the backscatter modulation waveforms. The modulated signal appears across the RF coils, as shown in (2005) and is received by an external receiver. The modulating signal is shown in (2010). When this signal is low, the rectifier consumes major part of the current as shown in (2015). Whereas, when this signal is high, the backscatter switch sinks almost all of the current as shown in (2020), and produces the required modulation on the RF signal.

Figure 21:
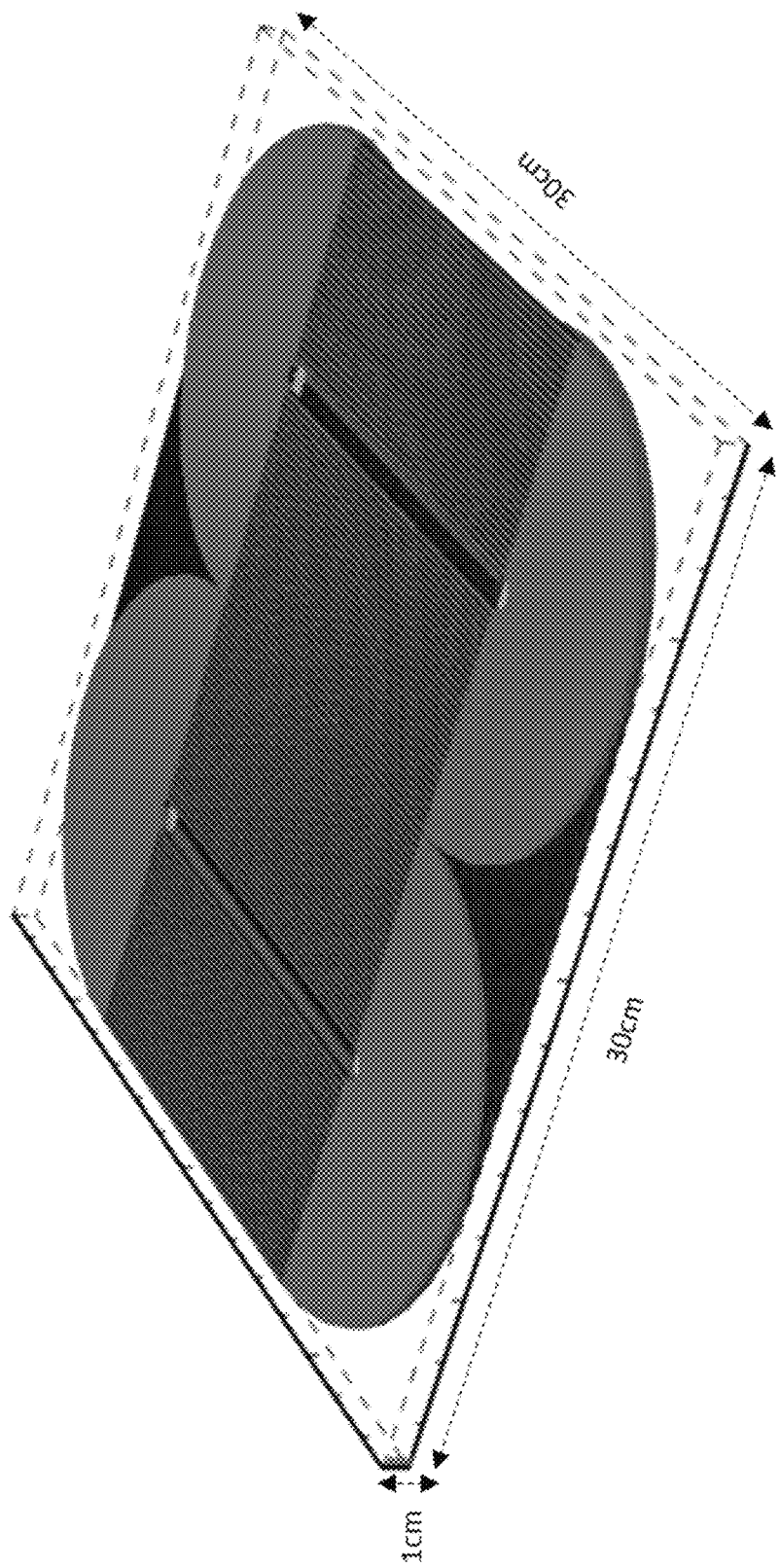
FIGS. 21-22 illustrate exemplary coils.
Figure 22:
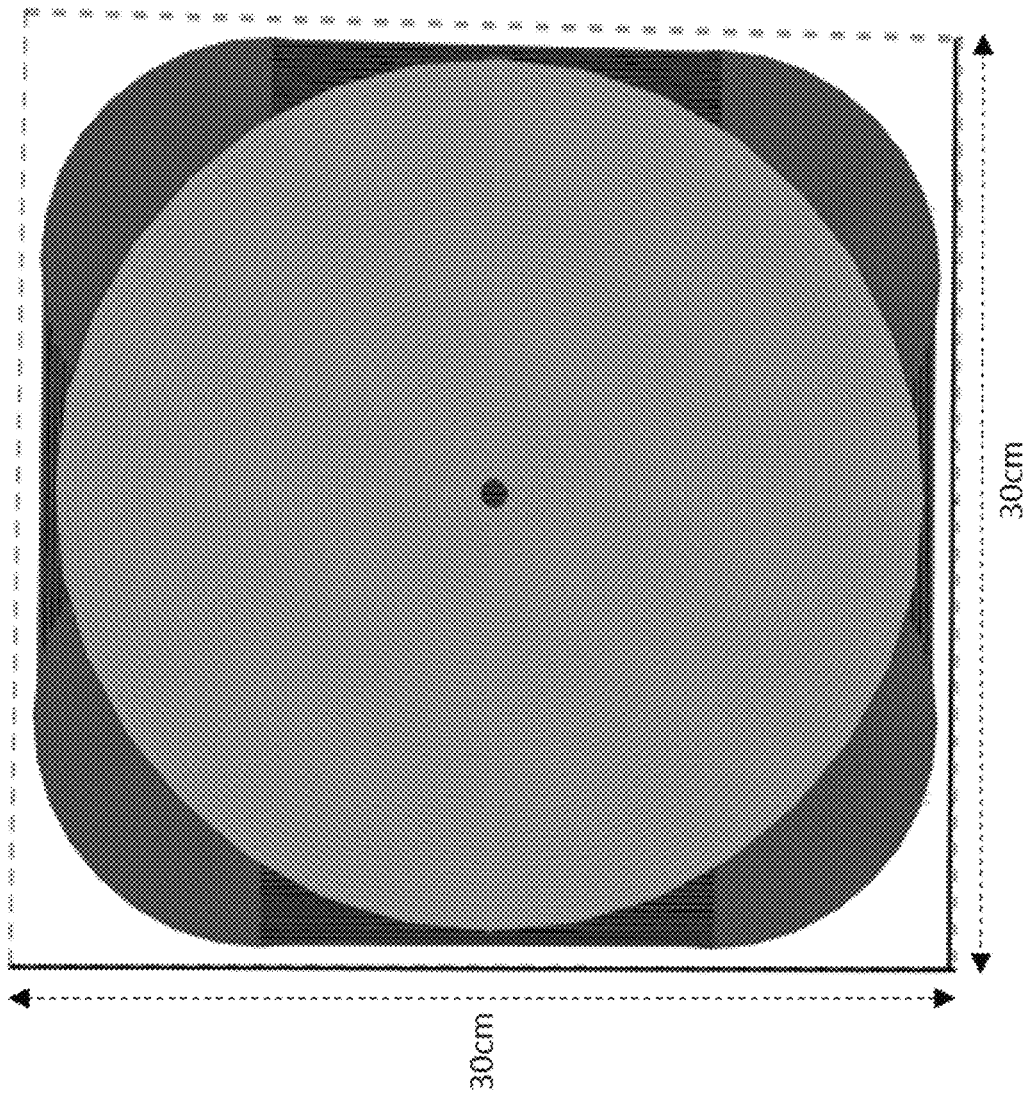

In some embodiments, the magnetic field gradient coils needs to produce a field gradient of 30 mT/m (in each direction) in order to achieve a spatial resolution of 100 μm for the given sensor resolution of 3.1 μT. It is possible to reduce the volume of the gradient coils drastically and obtain the above field values by using coils that measure 30 cm×30 cm×1 cm, as shown in FIGS. 21-22. FIG. 21 illustrates a top view of the coils, in perspective, while FIG. 22 illustrates the bottom view. This result was possible by increasing the current density for each coil setup, and by using higher current values.

Figure 23:
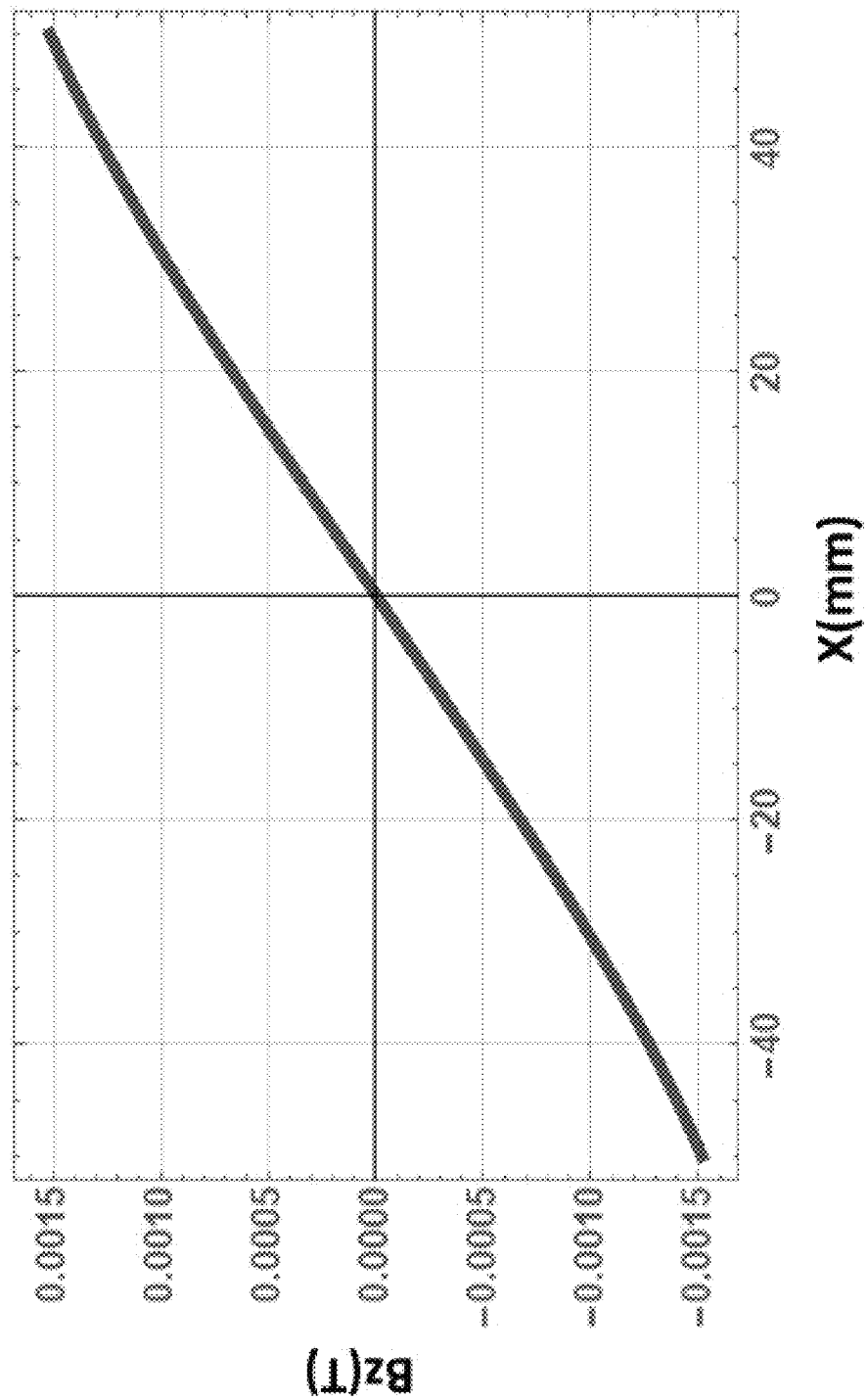
FIGS. 23-25 illustrate simulated field gradient plots.
Figure 24:
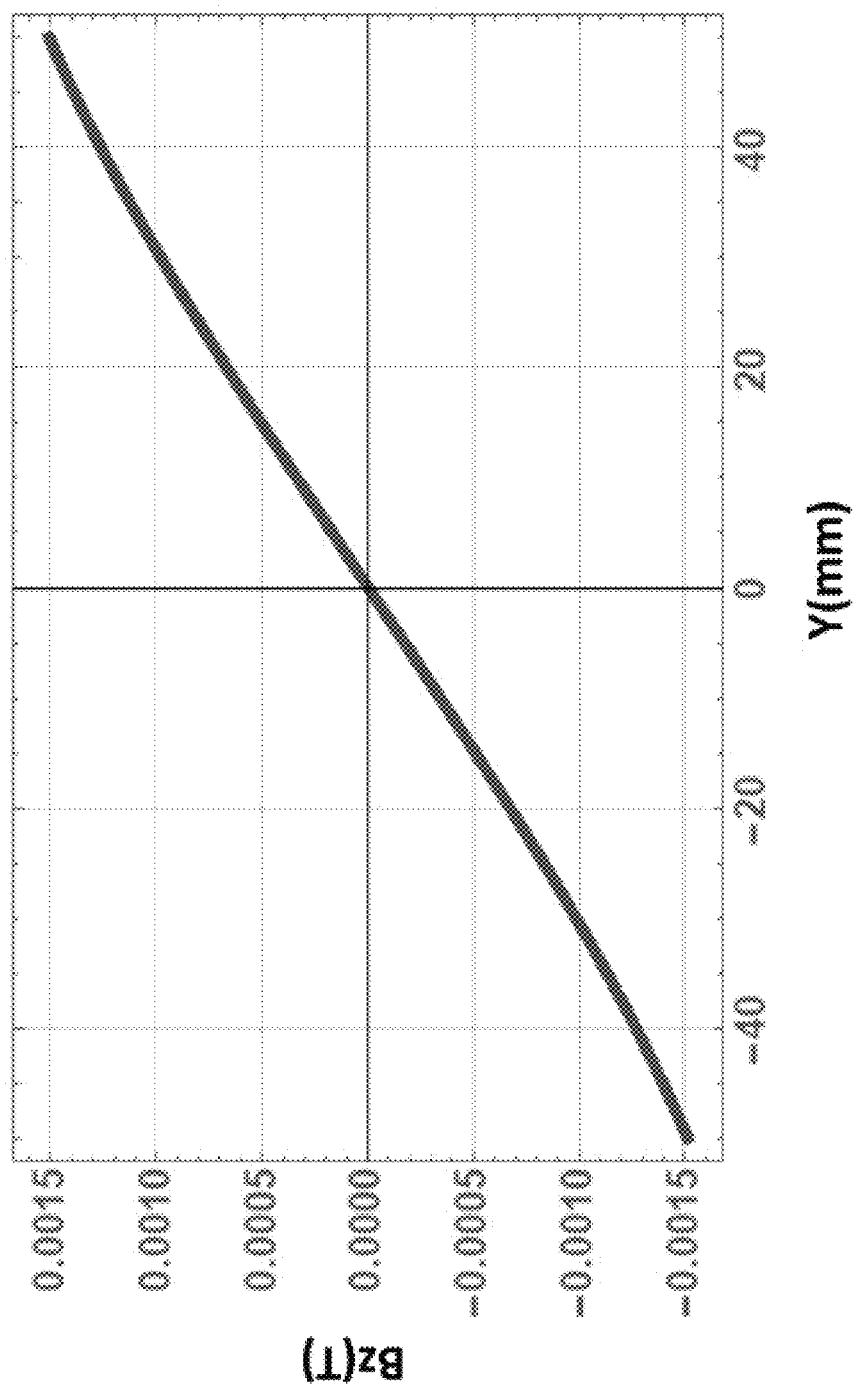
Figure 25:
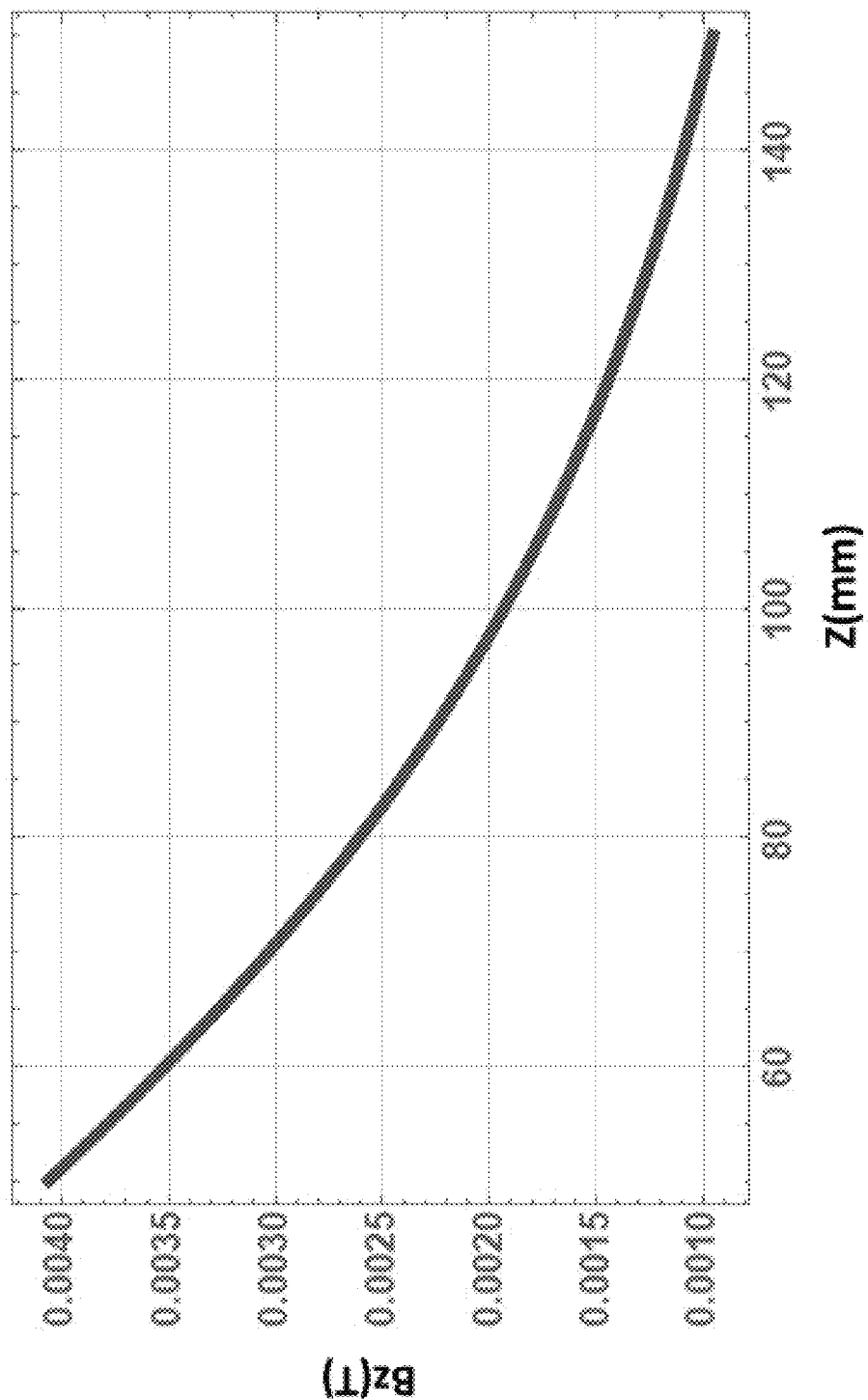

When the magnetic field gradients are simulated, it is observed that the x coils, in this example, need a current of 18 A, the y coils need 20 A, and the z coils need 13 A to generate a gradient of 30 mT/m in all three dimensions. The simulated gradient plots are shown in FIGS. 23-25. The high currents could generate serious heating issues for the coils. To avoid this problem time-multiplexing of the field measurement is carried out, which turns the gradient coils ON and produces a stable gradient for only 1 ms, the time needed by sensor to make a measurement. For the remainder of the time slot, which is approximately 80 ms in every time frame of 100 ms, the corresponding gradient coils are OFF and the heating effect is negligible. The 20 ms time window for which the coils are ON also takes into account the finite rise and fall time of the current, due to self-inductance of the coils.

Figure 26:
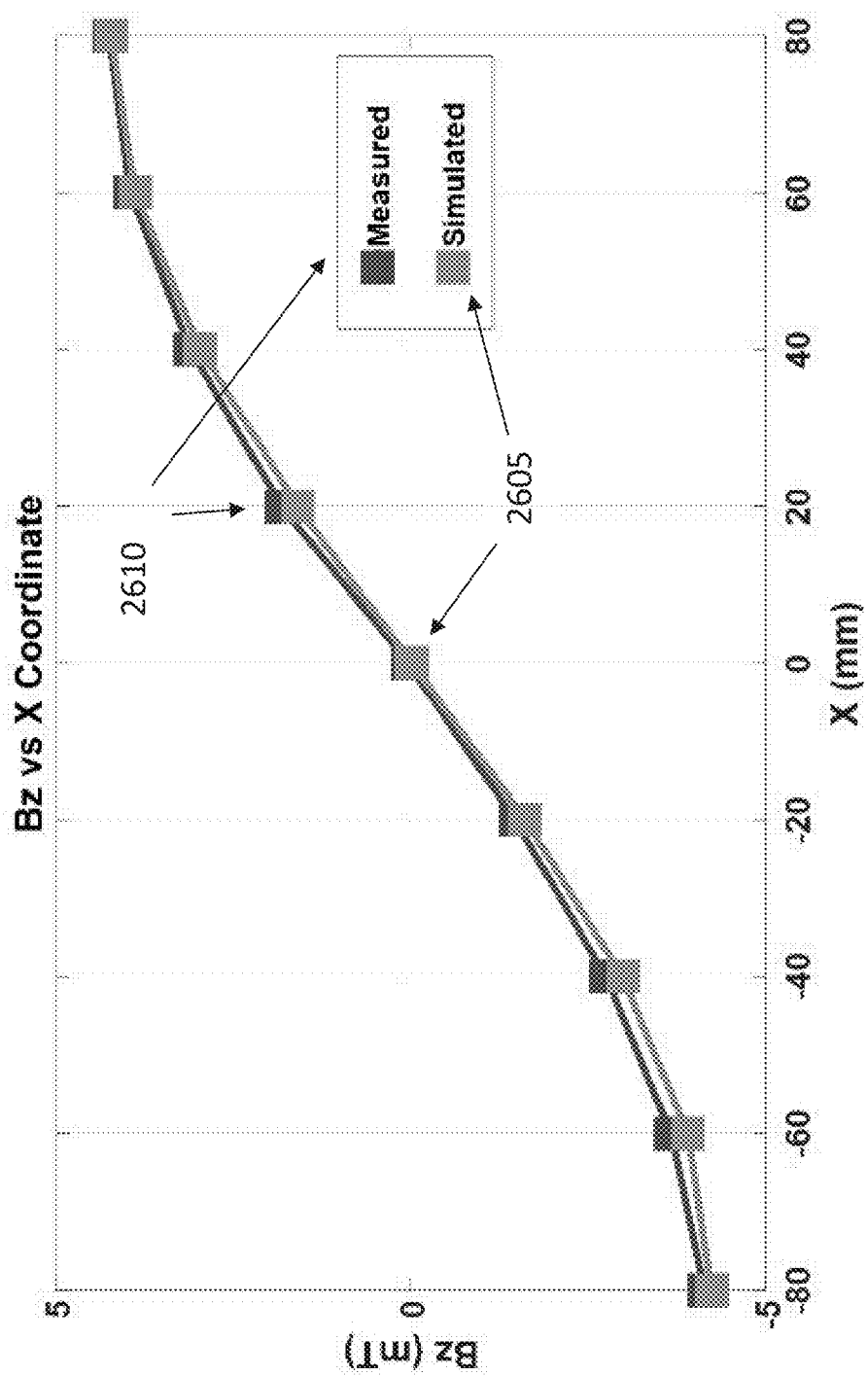
FIGS. 26 and 27 illustrate a comparison between simulated and measured field values for exemplary coils.
Figure 27:
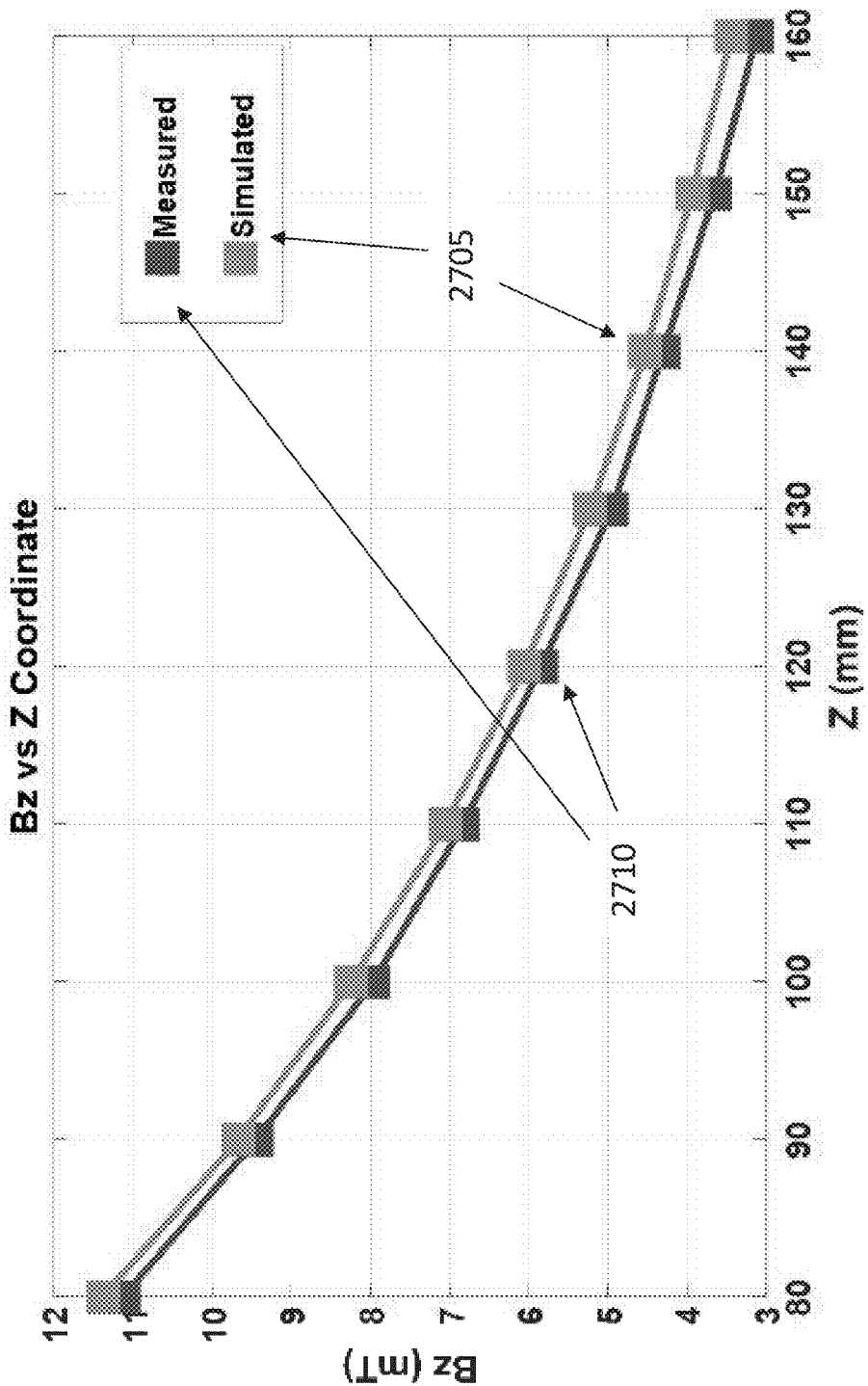

In some embodiments, the coils can be fabricated with litz wire. Litz wire is a specialized multistrand wire that reduces skin effects and proximity losses. The wire can be wound on a 3D printed plastic base. A very good match can be observed between the simulated (2605,2705) and measured (2610,2710) gradient profiles for exemplary coils fabricated as prototypes, as shown in FIGS. 26 and 27 for the z and x coils respectively. The gradient profile for the y coils was similar to that of the x coils. The magnetic sensors in the devices can detect three field components in three orthogonal axes. The system can display relative alignment and locations of the first and second sensors attached, for example, to a surgical nail for bone repair, and a surgical drill.

In some embodiments, the surgical device, e.g. the drill, can identify its location without the use of ATOMS, for example with gyroscopes or optical positioning, while the nail is located using ATOMS. In some embodiments, the surgical device does not transmit its data wirelessly, but it is instead wired to the computer or the display.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A method comprising:
providing a system comprising:
a first sensor configured to be inserted in a patient during a surgical procedure, the first sensor comprising:
a first magnetic sensor configured to detect a first magnetic field value,
a first integrated circuit chip configured to process data from the first magnetic sensor, and
a first radiofrequency coil configured to transmit data processed by the first integrated circuit chip based on the first magnetic field;
a second sensor attached to a surgical instrument, the second sensor comprising:
a second magnetic sensor configured to detect a second magnetic field value, and
a second integrated circuit chip configured to process data from the second magnetic sensor;
generating, by a plurality of coils, a magnetic field gradient within a volume in which the surgical procedure takes place, wherein the magnetic field gradient has a unique field value at each spatial location;
sensing, by the first sensor, a first location of the first sensor based on the magnetic field gradient;
sensing, by the second sensor, a second location of the second sensor based on the magnetic field gradient;
displaying, on a display, the first and second locations, and a relative alignment between the first location and the second location; and
aligning the surgical instrument based on the displayed relative alignment;
wherein the plurality of coils comprises at least:
a first elliptical x coil and a second elliptical x coil configured to accept currents flowing in opposite directions to each other;
a first elliptical y coil and a second elliptical y coil configured to accept currents flowing in opposite directions to each other, the first and second elliptical y coils laying in a plane parallel to the first and second elliptical x coils, and rotated 90° relative to the first and second elliptical x coils; and
a z coil.

2. The method of claim 1, wherein the first sensor is attached to a surgical nail, the second sensor is attached to a surgical drill, and the aligning the surgical instrument comprises aligning of the surgical drill and of the surgical nail.

3. The method of claim 1, wherein the second sensor further comprises a second radiofrequency coil configured to transmit data processed by the second integrated circuit chip based on the second magnetic field.

4. The method of claim 1, wherein the first magnetic sensor further comprises a battery.

5. The method of claim 1, wherein the first radiofrequency coil of the first magnetic sensor is further configured to wirelessly receive power.

6. The method of claim 1, wherein the first magnetic sensor and the second magnetic sensor are Hall sensors configured to sense three field components in three orthogonal axis, and the magnetic field gradient is monotonic.

7. A method comprising:
  providing a system comprising:
    a first sensor configured to be inserted in a patient during a surgical procedure, the first sensor comprising:
      a magnetic sensor configured to detect a first magnetic field value,
      an integrated circuit chip configured to process data from the magnetic sensor, and
      a radiofrequency coil configured to transmit data processed by the integrated circuit chip based on the first magnetic field;
    a surgical instrument; and
    a second sensor configured to sense a location of the surgical instrument relative to the first sensor;
  generating, by a plurality of coils, a magnetic field gradient within a volume in which the surgical procedure takes place, wherein the magnetic field gradient has a unique field value at each spatial location;
  sensing, by the first sensor, a first location of the first sensor based on the magnetic field gradient;
  sensing, by the second sensor, a location of the surgical instrument relative to the first sensor;
  displaying, on a display, the first and second locations, and a relative alignment between the first location and the second location; and
  aligning the surgical instrument based on the displayed relative alignment;
  wherein the plurality of coils comprises at least:
    a first elliptical x coil and a second elliptical x coil configured to accept currents flowing in opposite directions to each other;
    a first elliptical y coil and a second elliptical y coil configured to accept currents flowing in opposite directions to each other, the first and second elliptical y coils laying in a plane parallel to the first and second elliptical x coils, and rotated 90° relative to the first and second elliptical x coils; and
    a z coil.

8. The method of claim 7, wherein the second sensor comprises a gyroscope attached to the surgical instrument, or an optical positioning device.

9. The method of claim 7, wherein the first magnetic sensor further comprises a battery.

10. The method of claim 7, wherein the first radiofrequency coil of the first magnetic sensor is further configured to wirelessly receive power.

11. The method of claim 7, wherein the first magnetic sensor and the second magnetic sensor are Hall sensors configured to sense three field components in three orthogonal axis, and the magnetic field gradient is monotonic.

* * * * *